(12) United States Patent
Lee

(10) Patent No.: US 9,186,049 B2
(45) Date of Patent: Nov. 17, 2015

(54) EXTENSIBLE AND GUIDABLE APPARATUS

(71) Applicant: Choon Kee Lee, Denver, CO (US)

(72) Inventor: Choon Kee Lee, Denver, CO (US)

( * ) Notice: Subject to any disclaimer, the term of this patent is extended or adjusted under 35 U.S.C. 154(b) by 434 days.

(21) Appl. No.: 13/660,970

(22) Filed: Oct. 25, 2012

(65) Prior Publication Data
US 2014/0118515 A1    May 1, 2014

(51) Int. Cl.
| | |
|---|---|
| *A61B 1/04* | (2006.01) |
| *A61B 1/00* | (2006.01) |
| *A61B 1/005* | (2006.01) |
| *G02B 23/24* | (2006.01) |
| *A61B 1/12* | (2006.01) |
| *A61B 17/00* | (2006.01) |

(52) U.S. Cl.
CPC ............ *A61B 1/0055* (2013.01); *A61B 1/00151* (2013.01); *A61B 1/12* (2013.01); *G02B 23/2476* (2013.01); *A61B 1/00052* (2013.01); *A61B 1/00114* (2013.01); *A61B 2017/00305* (2013.01)

(58) Field of Classification Search
CPC .......................... A61B 1/00052; A61B 1/0008
USPC ................... 348/65; 600/104, 139, 141–150
See application file for complete search history.

(56) References Cited

U.S. PATENT DOCUMENTS

| | | | |
|---|---|---|---|
| 4,176,662 A | 12/1979 | Frazer | |
| 5,179,934 A | 1/1993 | Nagayoshi | |
| 5,259,364 A | 11/1993 | Bob | |
| 6,875,170 B2 * | 4/2005 | Francois et al. | ............... 600/141 |
| 6,899,674 B2 | 5/2005 | Viebach | |
| 6,951,573 B1 | 10/2005 | Hirata | |
| 6,988,988 B2 | 1/2006 | Voloshin | |
| 7,022,068 B2 | 4/2006 | Kim | |
| 7,056,283 B2 | 6/2006 | Baror | |
| 7,214,183 B2 * | 5/2007 | Miyake | .......................... 600/131 |
| 7,264,588 B2 * | 9/2007 | Voloshin et al. | ............... 600/115 |
| 7,988,621 B2 | 8/2011 | Smith | |
| 8,092,374 B2 | 1/2012 | Smith | |
| 2006/0183974 A1 | 8/2006 | Levy | |
| 2006/0252989 A1 | 11/2006 | Bar-Or | |
| 2007/0055102 A1 | 3/2007 | Hirata | |
| 2007/0225556 A1 * | 9/2007 | Ortiz et al. | ..................... 600/109 |
| 2007/0249906 A1 * | 10/2007 | Gorini et al. | ................... 600/139 |

(Continued)

FOREIGN PATENT DOCUMENTS

| | | |
|---|---|---|
| GB | WO9811816 A1 | 3/1998 |
| JP | 2009066145 A | 2/2009 |
| JP | 2009061173 A | 3/2009 |

*Primary Examiner* — Anhtuan T Nguyen
*Assistant Examiner* — Timothy J Neal

(57) ABSTRACT

The current invention presents an extensible and guidable apparatus and methods to evaluate tubular or cavitary structure. The apparatus has a power, control and display unit and a flexible tubular device having a proximal end and a distal end. A stretchable conduit and a plurality of extensible channels run longitudinally inside the flexible tubular device. The flexible tubular device comprises a non-extensible tubular shaft and a reversibly extensible tubular shaft, connected longitudinally in tandem. The reversibly extensible tubular shaft comprises a plurality of reversible extension segments and is controllably longitudinally extensible and bendable by changes in pressure and volume of a medium in said reversible extension segments. Said tubular device is directionally bendable at the distal end by selective negative changes in pressure in said distal end. Said tubular device obtains visual information of target area and material samples, and is capable of manipulation of the target area.

26 Claims, 19 Drawing Sheets

(56) References Cited

U.S. PATENT DOCUMENTS

2008/0275299 A1 11/2008 Park
2009/0137869 A1* 5/2009 Soutorine et al. ............ 600/114
2010/0256445 A1 10/2010 Fitzpatrick
2011/0060186 A1* 3/2011 Tilson et al. ................. 600/104
2011/0105846 A1 5/2011 Yoshi

* cited by examiner

Figure 11

|      | p16p | p17p | p16d | p17d |
|------|------|------|------|------|
| 31B  | 50   | 50   | 30   | 30   |
| 31B  | 50   | 50   | 30   | 30   |
| 31C  | 52   | 50   | 48   | 30   |
| 31C  | 52   | 50   | 48   | 30   |
| 31D  | 50   | 52   | 50   | 48   |
| 31D  | 50   | 52   | 50   | 48   |

Figure 12

| Mode | Direction | No of Channels | 1st Channel | | 2nd Channel | | 3rd Channel | | 4th Channel | |
|---|---|---|---|---|---|---|---|---|---|---|
| | | | OP | MP | OP | MP | OP | MP | OP | MP |
| A: Extend & Bend -1st Segment- | Linear | | 50 | 50 | 50 | 50 | 50 | 50 | 50 | 50 |
| | Bending | 1 Channel | 50 | 50 | 48 | 48 | 50 | 50 | 50 | 50 |
| | Bending | 2 Channels | 50 | 50 | 48 | 48 | 48 | 48 | 50 | 50 |
| | Bending | 3 Channels | 50 | 50 | 48 | 48 | 48 | 48 | 48 | 48 |
| B: Vent to next segment -1st Segment- | Linear | | 54 | 50 | 54 | 50 | 54 | 50 | 54 | 50 |
| | Bending | 1 Channel | 54 | 50 | 52 | 48 | 54 | 50 | 54 | 50 |
| | Bending | 2 Channels | 54 | 50 | 52 | 48 | 52 | 48 | 54 | 50 |
| | Bending | 3 Channels | 54 | 50 | 52 | 48 | 52 | 48 | 52 | 48 |
| C: Pressure equalization for linear extension -2nd Segment- | | | 48 to 50 | 48 to 50 | 48 to 50 | 48 to 50 | 48 to 50 | 48 to 50 | 48 to 50 | 48 to 50 |
| D: Extend & Bend -2nd Segment- | Linear | | 50 | 50 | 50 | 50 | 50 | 50 | 50 | 50 |
| | Bending | 1 Channel | 48 | 48 | 50 | 50 | 50 | 50 | 50 | 50 |
| | Bending | 2 Channels | 48 | 48 | 48 | 48 | 50 | 50 | 50 | 50 |
| | Bending | 3 Channels | 48 | 48 | 48 | 48 | 48 | 48 | 50 | 50 |
| E: Vent to next segment -2nd Segment- | Linear | | 54 | 50 | 54 | 50 | 54 | 50 | 54 | 50 |
| | Bending | 1 Channel | 52 | 48 | 54 | 50 | 54 | 50 | 54 | 50 |
| | Bending | 2 Channels | 52 | 48 | 52 | 48 | 54 | 50 | 54 | 50 |
| | Bending | 3 Channels | 52 | 48 | 52 | 48 | 52 | 48 | 54 | 50 |
| F: Pressure equalization for linear extension -3rd Segment- | | | 48 to 50 | 48 to 50 | 48 to 50 | 48 to 50 | 48 to 50 | 48 to 50 | 48 to 50 | 48 to 50 |

EXTENSIBLE AND GUIDABLE APPARATUS

CROSS REFERENCE TO RELATED APPLICATIONS

Attached please refer to the Information Disclosure Statement for the cross reference to related applications.

STATEMENT REGARDING FEDERALLY SPONSORED RESEARCH OR DEVELOPMENT

The present invention is not a federally sponsored research or development.

TECHNICAL FIELD

The present invention relates generally to the field of evaluation of tubular or cavitary structure by endoscope for medical and industrial purpose. More specifically, the present invention provides an extensible endoscopic apparatus and methods to evaluate tortuous and extended tubular structure.

BACKGROUND OF THE INVENTION

Evaluating a long, closed and inaccessible structure of machines or an internal hollow viscus of a living body without surgical methods has been greatly improved by development of flexible endoscopic apparatus that can be inserted into the closed structure of the machine or the hollow viscus under direct visual guidance. For evaluation of human body, it allows critical visual inspection of inner structure of the hollow viscus and guided procedures such as obtaining tissue samples and surgical procedures using insertable instruments. Endoscopic procedures now have become an essential component of evaluation and treatment of diverse pathologies of the hollow viscus of the body. For an example, inspection of colon by a colonoscope is universally required as a screening tool for early detection of colon cancer in the Western countries. Similarly, gastroduodenoscope is being used for screening stomach cancer in Asian countries.

Endoscopic apparatus in general comprises a distal end that is bendable by internal guide-wires, a proximal end that controls the distal end by the guide-wires and a tubular shaft that houses internal conduits and connects both ends. Image of a target area is acquiesced electronically by an image sensor that is attached to an optic lens complex of the distal end and is connected to the proximal end and a power and control unit via longitudinally linear electric cables. The optic lens complex at the distal end is cleansed by water for clear view of a target area. Gas such as air is insufflated to the target area for three dimensional expansion of the area and negative suction is applied to the target area to remove unwanted fluids and gas. Water, gas and negative suction are provided through longitudinally linear tubular conduits connected to the distal end. Instrumentation of devices such as biopsy forceps is done through a linear tubular channel that runs from a hub located at the proximal end to the distal end.

Bending of a tubular shaft of an endoscope usually is achieved by linear pull-strings that run longitudinally inside the tubular wall from control knobs of the proximal end to internal bending anchors of the distal end. There is no active bending action outside the bendable segment of the distal end. The tubular shaft between the bendable segment and the proximal end usually is flexible to a certain degree, allowing it to passively curve inside the tubular structure. Forward movement of the distal end of an endoscope usually is achieved by manually pushing the proximal end into the tubular structure.

The aforementioned endoscope accordingly has a structure of a hollow tube of a fixed length in which a number of hollow tubular conduits and channels of a similarly fixed length are longitudinally placed, between the two opposite ends. Main advantages of said endoscope include real-time maneuverability, its access to target tissues of the majority of the tubular structure of a living body and most importantly its capability to obtain biologic samples and to manipulate the target area under direct vision. Main disadvantages of said endoscope come from its inability to navigate in a meandering tubular structure such as a zigzagging small intestine and its fixed length beyond which no further evaluation could be achieved. Capsular endoscopic instruments are developed to circumvent the need to navigate in the zigzagging small intestine without length limitation. These devices can be swallowed and be let tumble down through the tortuous small intestine, while acquiescing digital visual information of said intestine. One most significant drawback of said capsular endoscopes, however, is the most critical, which is their inability to obtain a sufficient amount of biologic samples and to manipulate the target area. As a result, capsular endoscopes usually are used for screening purpose. If abnormalities are found in the deep part of said small intestine that cannot be reached by existing tubular endoscopes, further evaluation and therapy may only be achievable through direct surgery.

Difficulties in forward movement of a distal end of an endoscope in said zigzagging small intestine come from its dependence on passive forward push from the proximal end and presence of opposite directions of segments of the small intestine in contrast to a large intestine that can be considered as one continuous arc that can be reached by one direction of forward movement. Bending of a bendable part of the distal end alone may not allow passage of a tubular shaft of the endoscope through the zigzagging small intestine since the tubular shaft usually has a fixed directional flexibility that may not be changed simultaneously at points of opposite direction. These technical challenges may be offset by devices that control flexibility of the shaft while generating active forward movement at the site of changes in direction. Generating forward zigzagging movement of said shaft along a contour of the meandering small intestine could further enhance navigation of said tubular device toward a target area in an otherwise inaccessible location.

Controllable flexibility at a site of forward movement of a segment of a tubular shaft may be achievable if the segment of the shaft is made longitudinally extend or contract and made bend by pressure changes inside the segment. A medium such as gas or liquid including gaseous phase of liquid is delivered into the segments of the tubular shaft by a power and control unit. The medium occupies an inner space in the tubular shaft of the endoscope and/or can be localized in predefined longitudinal spaces along the tubular shaft. Volume and pressure of the medium can be changed by the power and control unit and said changes in the volume and pressure translate into changes in length of the segments and generate differences in outward radial tension on walls of the segments of the shaft.

One other technical challenge in a tubular shaft that controllably varies in length is that channels and conduits inside the tubular shaft should be made vary in length together with changes in length of the tubular shaft. Electric cables for the electronic image sensor and other components can be coiled telephone-cord-like inside the tubular shaft, which extends by longitudinal stretching. Internal conduits for water, gas and suction may also be made in a similar way, which may all be consolidated with the electric cables in one telephone-cord-like coil. The telephone-cord-like coil then connects the power and control unit to the distal end, with its pitches and diameter of the coil dependent on a ratio of straightened state to coiled state and on an internal diameter of the tubular shaft. Internal channel for instruments, however, requires longitudinally straight configuration from the proximal end to the distal end to allow passage of instruments without mechanical hindrance. Longitudinally linear bellows-shaped construction of the channel may accomplish the goal, which contracts and extends along the longitudinal axis of the channel.

Forward axial movement of the distal end may best be achieved by longitudinal extension of segments of a tubular shaft located proximal to the distal end. Ideally, segments of the shaft may be extended sequentially, starting from the most proximal segment to the most distal segment that is attached to the distal end. Sequential segmental extension may accommodate differences in linear length of an intestine in between of two opposite curves of the intestine, in radii of curves of the intestine and in direction of the curves.

SUMMARY OF THE INVENTION

The present invention describes an apparatus of devices and methods for evaluation and manipulation of tubular or cavitary structure for medical and industrial purpose. A noble flexible tubular device is inserted into the tubular or cavitary structure through natural openings and orifices or surgically created openings and channels. The tubular device controllably extends longitudinally and bends along the axis of a tubular shaft of said device by changes in pressure and volume of a medium filled inside the tubular shaft. The tubular device curves along curvature of the tubular structure by reversibly adjusting flexibility and curving radius of individual segments of the tubular shaft. A distal end of the tubular device is made controllably bendable for directional guidance by a separate set of changes in pressure and volume from changes in pressure and volume of the medium for the tubular shaft.

In one embodiment, the flexible tubular device is pressure-sealed and comprises a bendable distal end, a proximal end, and a main tubular shaft connecting both said ends. The main tubular shaft has a non-extensible part and a reversibly extensible part, arranged in tandem. The reversibly extensible part is connected proximally to the distal side of the non-extensible part and distally to the proximal side of the distal end. The non-extensible part is connected proximally to the proximal end that is connected to a power, control and display (PCD) unit via a connecting tubular shaft. The PCD unit provides the main tubular shaft and the distal end with electricity, water, gas and negative suction via a plurality of stretchable conduits that are connected between the PCD unit and the distal end. The stretchable conduits are configured as one spiral-coil conduit of a plurality of longitudinally adhered conduits. The PCD unit also provides the tubular device with a medium of either gas or liquid including gaseous phase of liquid through the connecting tubular shaft. The medium is supplied under a range of pressure that is reversibly adjustable by the PCD unit.

In one embodiment, the bendable distal end is configured as a longitudinal cylindrical tube that is reversibly bendable by negative changes in pressure and volume in the cylindrical tube. A distal end cap of the bendable distal end has openings of a straightened portion of the stretchable spiral-coiled conduit for light, gas and water source. One of the openings has an image acquisition complex that comprises an optic lens complex, a charged-couple device (CCD) image sensor and a light source such as a plurality of light emitting diodes (LED). The optic lens complex is attached to the CCD image sensor that picks up digitized visual information of a target area illuminated by a plurality of the LED. The LED is connected to the PCD unit via electric cables to generate light and the CCD image sensor is connected to the PCD unit and to an electronic display of the proximal end via electric cables running inside the stretchable spiral-coiled conduit. Both water and gas are delivered to a target area through the stretchable conduit from the PCD unit, which is controllable by knobs located at the proximal end. One of the openings connected to one of the conduits of the stretchable spiral-coiled conduit may serve for suctioning contents of the target area to a collection chamber located in the PCD unit.

In one embodiment, immediately proximal to the distal end cap of the bendable distal end, a doughnut-shaped solenoid assembly may be provided in circular configurations around a longitudinal axis, through which the stretchable spiral-coiled conduit pass toward the tip of the distal end. The solenoid assembly is connected to the PCD unit via electric cables and is to reversibly produce a plurality of static electromagnetic fields around said solenoid assembly. The electromagnetic fields reversibly interact with a plurality of magnetized instruments that pass through an extensible bellows-shaped channel from the proximal end to the distal end, in ways to push and retrieve a distal tip of the instruments for intended procedures.

In one embodiment, the bendable distal end is configured as concentric cylindrical tube-in-tube in a longitudinal axis between the distal end cap of the distal end and a distal end joint. The concentric cylindrical tube-in-tube configuration comprises an outer wall, a corrugated mid wall that is collapsible along a longitudinal axis and a corrugated inner wall that is also collapsible along the longitudinal axis. The outer wall is configured as one uninterrupted circumferential hollow tubular wall. The collapsible corrugated mid wall is irreversibly adhered to the outer wall in a circumferential direction at a right angle to the longitudinal axis. The corrugated inner wall forms a hollow tube through which the straightened portion of the stretchable spiral-coiled conduit and the extensible bellows-shaped channels pass toward the distal end cap of the distal end. In between of both said mid and inner wall, there is provided a chamber that is filled with a medium such as gas or liquid. The chamber is doughnut-shaped in a circumferential axis and cylindrically tubular in the longitudinal axis. The chamber may evenly be divided longitudinally along the axis by a plurality of longitudinal cylindrical gaps into a plurality of separated chambers. The hollow tube bordered by the collapsible corrugated inner wall forms an inner tubular chamber.

In one embodiment, a proximal side of the bendable distal end is attached to a segment of the main tubular shaft via a distal end joint. The distal end joint circumferentially affixes wall components of both the main tubular shaft and distal end to both sides of said joint. The distal end joint has a plurality of linear tunnels along the longitudinal axis, which accommodate a straightened portion of the stretchable spiral-coiled conduit and a straightened portion of the extensible bellows-shaped channels. The distal end joint also has a plurality of obtusely placed tunnels radially projecting from a central portion of the proximal side of the distal end joint to a circumferentially peripheral area on the distal side. The obtusely placed tunnels connect part of the stretchable spiral-coiled conduit on the proximal side to a plurality of separated chambers of the bendable distal end, matching each conduit with each tunnel and with each separated chamber. Said connection establishes an open communication between the part of the stretchable spiral-coiled conduit and the separated chambers. The inner tubular chamber of the distal end is a closed space bordered proximally by the distal end joint and distally by the distal end cap.

In one embodiment, the PCD unit draws the medium out of the plurality of chambers of the distal end thereby generating negative differences in pressure and volume in said plurality of chambers from the pressure of the medium filling the inner tubular chamber of the distal end. Said pressure differences of each separated chamber of the distal end may be differently negative, compared to each other. One or a plurality of the separated chambers can have a more negative pressure and volume than the rest of the separated chambers, which collapses and shortens at least one part of the collapsible corrugated inner wall of said separated chamber(s) along the longitudinal axis. The shortening produces longitudinal length differences between at least one part of the corresponding inner wall and the rest of the inner wall. Bending of the distal end along the longitudinal axis occurs consequent to the length differences.

In one embodiment, the inner tubular space of the main tubular shaft maintains a range of pressure of the medium, regulated by the PCD unit. The PCD unit generates pressure to the medium filled in said inner tubular space to control longitudinal flexibility of the main tubular shaft.

In one embodiment, the reversibly extensible part of the main tubular shaft comprises a plurality of reversible extension segments arranged in tandem along the longitudinal axis from the distal side of the non-extensible part of the main tubular shaft to the proximal side of the distal end joint. A reversible extension segment is configured as a hollow cylindrical tube, and comprises a plurality of tubular walls, an extension-spring-type coil circumferentially disposed inside an outer tubular wall along the longitudinal axis and a junction unit on both proximal and distal tubular ends along the longitudinal axis. The tubular walls are made of non-elastomeric polymeric materials. The tubular walls and the extension-spring-type coil are attached to both the junction units. Tandem repetition of the reversible extension segment along the longitudinal axis completes construction of the reversibly extensible part of the main tubular shaft. The walls are configured as longitudinally corrugated with circumferential peaks and valleys for longitudinal stretching and shrinking. The extension-spring-type coil may comprise a plurality of polymeric and/or metallic components and maintains three dimensional cylindrical shape of the reversible extension segment, exerts recoil on both the proximal and distal junction units upon stretch and provides circumferential rigidity of said segment. The junction unit provides attachment for the walls and the extension-spring-type coil and regulates flow of the medium for differential pressure changes of said medium inside the main tubular shaft.

In one embodiment, the reversible extension segment comprises an outer tubular wall, an extension-spring-type coil inside the outer tubular wall and a junction unit on both ends. Said configuration with the single outer wall produces a single tubular channel. In this configuration, the reversible extensible segments extend simultaneously in all the reversible extensible segments by increases in pressure and volume of the medium inside said tubular channel. The pressure and volume of the medium determine overall lengthening and flexibility of the reversibly extensible tubular shaft. The flexibility of said tubular shaft is indirectly proportional to lengthening and radius of an individual reversible extension segment. A highly flexible extensible tubular shaft can be bent with a smaller radius at the expense of shorter lengthening of said extensible tubular shaft. A further lengthening of said tubular shaft requires more pressure and volume of the medium to further stretch the outer wall, which increases both rigidity and bending radius of said tubular shaft. A major advantage of the single tube configuration lies in simplicity of construction requiring only the outer wall and the extension-spring-type coil for extension and in ease of control of the reversibly extensible tubular shaft.

In another embodiment, the reversible extension segment is configured as concentric cylindrical tube-in-tube. The concentric cylindrical tube-in-tube configuration comprises at least an outer wall, a mid wall and an inner wall, running in parallel with each other along the longitudinal axis. Said concentric cylindrical tube-in-tube configuration produces at least three concentrically arranged tubular channels, with an outer channel formed between the outer and mid wall, a mid channel between the mid and inner wall and an inner central channel by the inner wall. For the concentric cylindrical tube-in-tube configuration, the extension-spring-type coil is placed in between of the outer and mid wall, preferably attached to an outer surface of the mid wall. In another embodiment, said outer and mid channels may evenly be divided longitudinally along the axis by a plurality of longitudinal cylindrical gaps into a plurality of separated channels.

In one embodiment, said channels are filled with a medium throughout entire longitudinal length from the PCD unit to the distal end joint. The PCD unit applies pressure to the medium and changes volume of the medium inside the channels by increasing the volume of the medium in said channels or by drawing the medium out said channels. Upon an increase in volume and/or pressure of the medium inside the channels, the circumferential peaks and valleys of the tubular walls stretch to a planar configuration. Upon a decrease in volume and/or pressure of the medium, the planar walls shrink back to the circumferential peaks and valleys. Both volume and pressure of the medium determine extent of lengthening and flexibility of the main tubular shaft.

In one embodiment, the junction unit regulates flow of the medium in and out of the outer and mid channels. The junction unit is configured as doughnut-shaped concentric cylindrical tube-in-tube cross-sectionally, having an outer junction cylindrical conduit and an inner junction cylindrical conduit longitudinally divided by a divider and running in parallel with each other, matched to the outer and inner channels of the reversible extension segment. On the proximal side of both the outer and inner junction cylindrical conduits, there is provided a T-shaped directional pressure valve assembly that opens to either the outer junction cylindrical conduit or the inner junction cylindrical conduit by tilting from a right angle position to the divider. Center of the T-shaped directional pressure valve is aligned with the divider. In another embodiment, the T-shaped directional pressure valve assembly can be preset for a range of pressure of the medium to tilt to open said valve. The T-shaped directional pressure valve assembly comprises a T-shaped valve, a valve harness with a valve sealing rim and a compression spring such as a Belleville-washer-type compression spring located distally to the valve and centrally aligned with the divider. The compression spring abuts the valve proximally and exerts a range of pressure to maintain the valve in closed position. Asymmetric compression of the compression tilts the T-shaped directional pressure valve to an open valve position by a pivoting motion of the center of the T-shaped valve. Accordingly compressibility of the compression spring can be preset for a range of pressure.

Flow, volume and pressure of the medium in both the outer and mid channels are differentially adjustable for each channel by the PCD unit. In this configuration, the reversible extension segments can extend sequentially from the most proximal segment to the most distal segment. If the PCD unit delivers the medium to both the outer and mid channels in a way to let both the channels maintain an equal pressure, the T-shaped directional pressure valve maintains its right angle position to the flow of the medium thereby blocking the flow of the medium. Further instillation of the medium while maintaining the equal pressure in both the outer and mid channels increases volume and pressure of said medium inside the outer and mid channels, which longitudinally extends both the outer and mid channels. Once the first reversible extension segment is stabilized as stretched and extended, the PCD unit delivers the medium differentially more to either the outer channel or the mid channel in a way to produce a pressure difference between the outer channel and the mid channel. The pressure difference of the medium upon the T-shaped directional pressure valve tilts said directional pressure valve to either the outer junction cylindrical conduit or the inner junction cylindrical conduit. Tilting of the directional pressure valve is configured as open valve, which allows passage of the medium to the channels of the second reversible extension segment. Repetition of the differential delivery of the medium to the outer and mid channels extends the second reversible extension segment.

In one embodiment, differential delivery of the medium to the outer and mid channels bends the reversible extension segment along the longitudinal axis. A junction unit is configured with a plurality of T-shaped directional pressure valves corresponding to a plurality of evenly divided outer and mid channels. Differential delivery of the medium under differential pressure to the plurality of outer and mid channels opens some T-shaped directional pressure valves while closing other T-shaped directional pressure valves. Simultaneous presence of open and closed T-shaped directional pressure valves allows extension of some channels while the other channels remain unchanged for longitudinal length. Discrepancy in the longitudinal lengths bends the reversible extension segment, which is regulated by changes in pressure and volume of the medium by the PCD unit.

In one embodiment, there is provided an non-extensible tubular shaft connected distally to a proximal side of the reversibly extensible tubular shaft, and proximally to the proximal end and to the PCD unit via a connecting tubular shaft of a certain length in a Y-shaped configuration. The non-extensible tubular shaft is configured as a passively flexible single hollow cylindrical tube along the longitudinal axis and is not extensible.

In one embodiment, an inner central tubular space longitudinally runs inside the main tubular shaft comprising the non-extensible hollow tubular shaft and the reversibly extensible tubular shaft connected in tandem, through which at least one stretchable spiral-coiled conduit passes from the PCD unit and at least one extensible bellows-shaped channel passes from a protruded housing of said bellows-shaped channel located on the side of the proximal end, respectively, to the distal end. The stretchable spiral-coiled conduit is made of a plurality of longitudinal non-collapsible polymeric cylindrical tubes which are concentrically adhered together. Extensible bellows-shaped channels are configured as longitudinally cylindrical bellows-shaped and are made of polymers that are non-collapsible. Extension ratio determined by a pitch and a diameter of the stretchable spiral-coiled conduit and longitudinal compression-to-expansion ratio of the bellows-shaped channel are determined in a way that a full extension of said stretchable spiral-coiled conduit and of said bellows-shaped channel accommodates a full longitudinal extension of the reversibly extensible tubular shaft from the junction with the non-extensible tubular shaft proximally to the distal end junction distally. An example of said configurations is illustrated in a following equation: An extension ratio A (a maximum extended length of a spiral-coiled conduit divided by a maximum coiled length of said spiral-coiled conduit) of a stretchable spiral-coiled conduit of a length B results in an A×B length upon full extension. A length of the main tubular shaft is calculated as a sum of a length C of the non-extensible tubular shaft and a length D of a full extension of the reversibly extensible tubular shaft. The length D of the fully extended reversibly extensible tubular shaft is calculated as an extension ratio E (a maximum extended length of a reversibly extensible tubular shaft divided by a maximum collapsed length of said extension tubular shaft) multiplied by a length F of said reversibly extensible tubular shaft in a collapsed configuration. Accordingly, the 'A×B' equals the 'C+D' and the 'D' equals the 'E×F'. In summary, the 'A×B' equals the 'C+E×F'.

In one embodiment, the outer wall of the reversible extension segments comprises a plurality of non-elastomeric thin planar polymeric sheets tightly stacked up and adhered to each other in a continuously circumferential way along the longitudinal axis of the tubular shaft. An outer sheet and an inner sheet may have circumferential grooves notched on said sheets, which is configured to allow circumferential folding of said sheets to produce circumferential peaks and valleys. In between of the outer and inner sheets, there is provided at least a middle sheet with embedded linear strings that run longitudinally along the longitudinal axis of the tubular shaft. The embedded linear strings are configured to provide the outer wall with structural and tensile support upon extending and collapsing movement.

In one embodiment, the proximal end comprises a longitudinal handle, control knobs and buttons, an electronic module for the control knobs and buttons, a digitized electronic display and a plurality of housings for bellows-shaped channels. The longitudinal handle houses said electronic module that is connected to the PCD unit via a plurality of electric cables. The control knobs and buttons are located on the longitudinal handle in a way that they can be accessed and controlled by one hand of an operator. The control knobs and buttons are configured to manipulate said tubular device for various function which at least includes forward advancement and retraction of the tubular shaft, bending of the tubular shaft, bending of the distal end, control of flexibility of the tubular shaft, delivery of water and gas to the target area, suctioning of material from the target area and image acquisition of the target area. The electronic display is located at the most proximal part of the proximal end and is configured to display electronically digitized images of the target area in real time. The housings for bellows-shaped channels are located on a tubular wall of the proximal end in a way instruments can be inserted into and retrieved from said channels. The housing is capped by a hub that is configured to seal pressure inside said housing.

In one embodiment, the PCD unit is configured to provide the tubular device with water, gas, shaft-filling medium and electricity. The PCD unit also provides suctioning of material from the target area. The PCD unit generates both positive and negative pressure for and both increase and decrease in volume of the medium and monitors pressure inside the tubular shaft. Separately, the PCD unit generates and monitors negative pressure for the medium filling the collapsible chambers of the distal end. The PCD unit produces light via a plurality of LED located at the distal end and relays electronically digitized images via electric cables from the CCD image sensor located at the distal end to both said PCD unit and the electronic display of the proximal end. The PCD unit is also configured to have a separate digitized electronic image monitor and to control the tubular device independently by a second operator or passively through input from the proximal end by the single operator who handles the tubular device.

BRIEF DESCRIPTION OF THE DRAWINGS

Overview shows a schematic presentation of the apparatus of the present invention.

FIG. 11 shows a table of an example of changes in pressure across T-shaped directional pressure valves for sequential extension, as illustrated in FIG. 10.

FIG. 12 shows an example of sequential pressure changes in tubular channels for extension and bending of concentric cylindrical tube-in-tube reversible extension segments.

DETAILED DESCRIPTION OF THE DRAWINGS

As described below, the present invention provides a number of devices and methods of use. It is to be understood that the descriptions are solely for the purposes of illustrating the present invention, and should not be understood in any way as restrictive or limited. Embodiments of the present invention are preferably depicted with reference to FIGS. 1 to 19, however, such reference is not intended to limit the present invention in any manner. The drawings do not represent actual dimension of devices, but illustrate the principles of the present invention.

The overview shows a schematic illustration of an example of the apparatus comprising a power, control and display (PCD) unit A and a pressure-sealed flexible tubular device B that is connected to the PCD unit A via a connecting tubular shaft G. The flexible tubular device B comprises a proximal end C, a non-extensible tubular shaft D, a reversibly extensible tubular shaft E and a distal end F. The non-extensible tubular shaft D is connected proximally to the proximal end C and distally to the reversibly extensible tubular shaft E. The reversibly extensible tubular shaft E has a plurality of reversible extension segments connected in tandem. The PCD unit A provides electricity, water, gas, negative suctioning and a medium filling the tubular device B, and controls the tubular device B.

Figure 1:
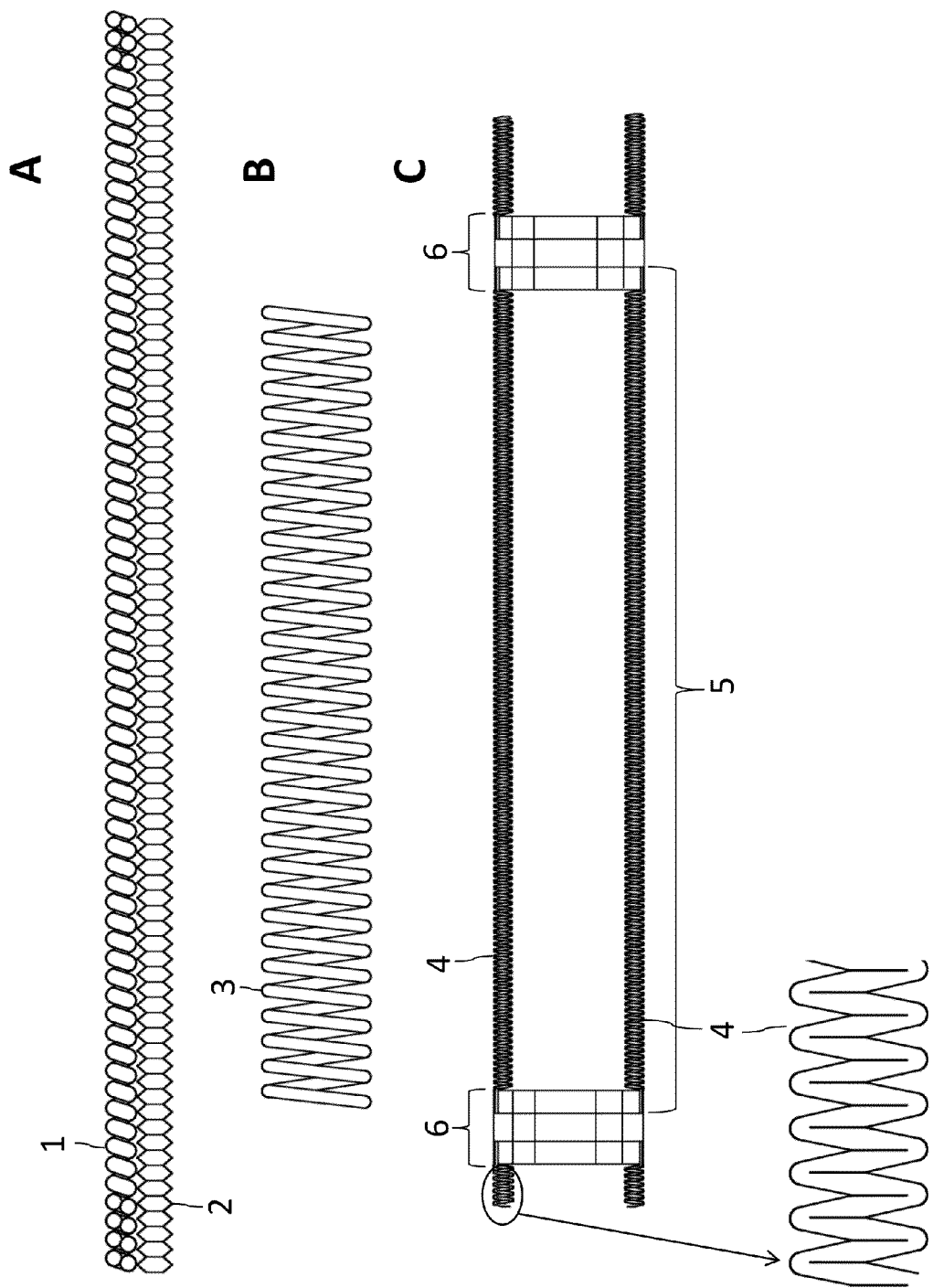
FIG. 1 shows a profile view of itemized components of a single tube-shaped reversible extension segment.
Figure 2:
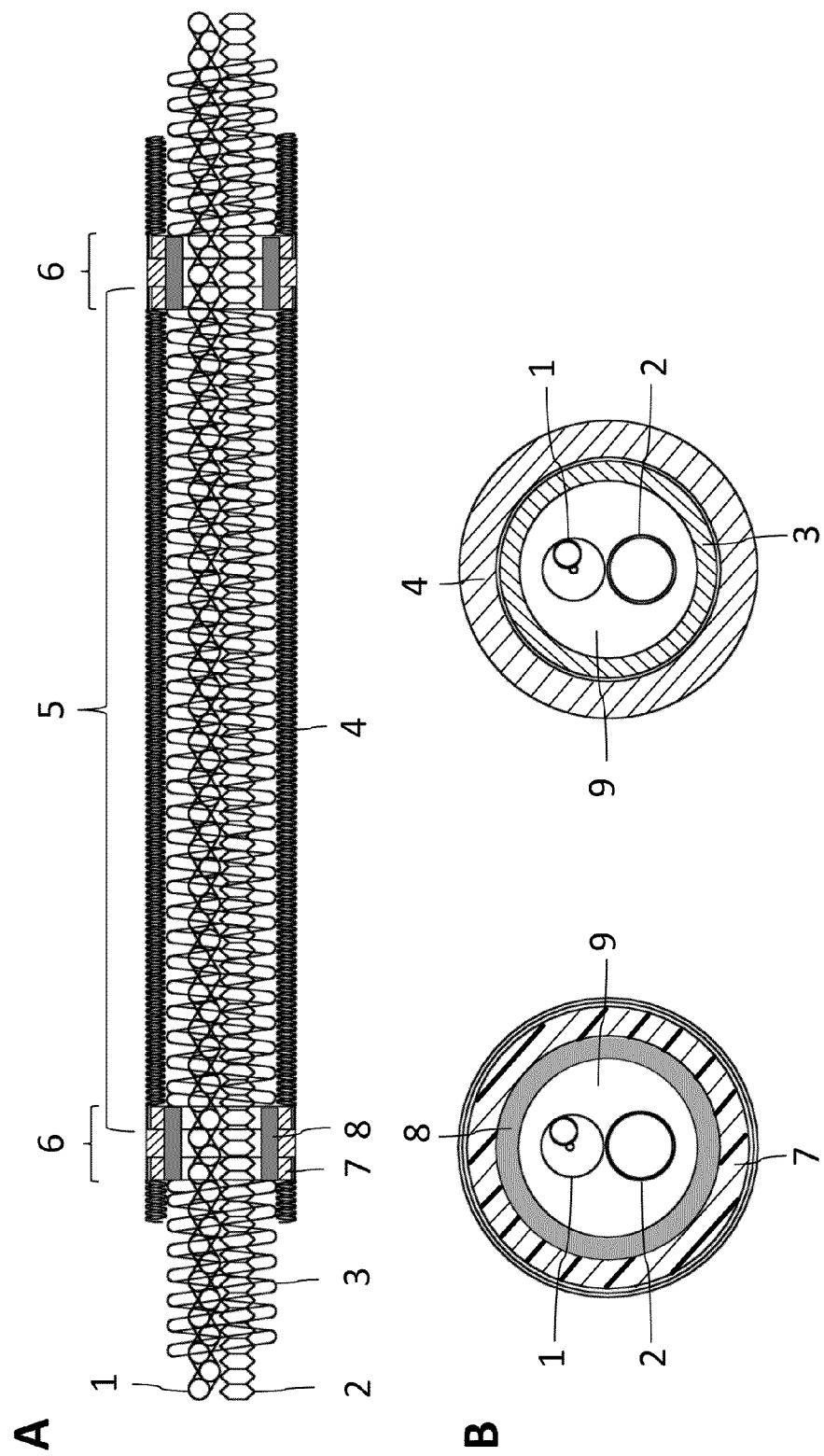
FIG. 2 shows a profile view and cross-sectional views of a single tube-shaped reversible extension segment with the itemized components assembled in one piece.

Referring to the reversible extensible tubular shaft E of the overview, FIG. 1 depicts individual components of a single tube-shaped reversible extension segment in a profile view. FIG. 1A shows a non-collapsible stretchable conduit 1 in a spiral-coiled configuration with both ends exposing two round outlines of said coiled conduits in each coiled loop. FIG. 1A also shows an extensible bellows-shaped channel 2 running longitudinally in parallel with the stretchable spiral-coiled conduit 1. FIG. 1B shows an extension-spring-type coil 3 that provides the reversible extension segment with circumferential structural rigidity, longitudinal flexibility and recoil upon extension. FIG. 1C shows a single unit of reversible extension segment 5 comprising an outer tubular wall 4. Both ends of the reversible extension segment 5 are connected to adjacent reversible extension segments via a junction unit 6. The outer tubular wall 4 is configured as circumferentially grooved with corrugation along the longitudinal axis and tightly stacked up in a neutral position, which can be stretched along the longitudinal axis.

Referring to FIG. 1, FIG. 2A shows a profile view of an assembled reversible extension segment 5. Inside the outer wall 4 that is non-elastomeric and stretchably corrugated, the extension-spring-type coil 3 is longitudinally inserted and attached to an anchor 8 on both proximal and distal sides of the junction unit 6. The junction unit 6 has a cylindrical outer rim 7 that provides said junction unit with structural support and irreversibly attaches to said outer wall 4. Both the extensible bellows-shaped channel 2 and the stretchable spiral-coiled conduit 1 run inside the extension-spring-type coil 3 along the longitudinal axis. FIG. 2B shows a cross-sectional view of the junction unit 6 and of the reversible extension segment 5. Inside said segment, there is provided an inner tubular space 9 that runs longitudinally along the axis.

Figure 3:
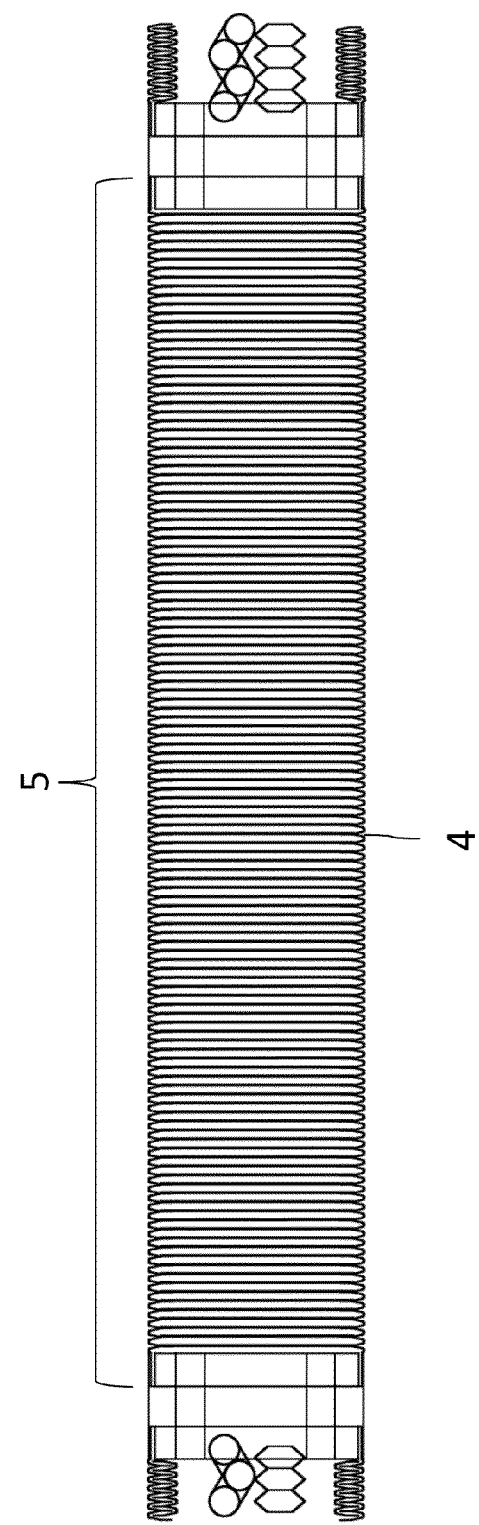
FIG. 3 shows a profile view of an exterior of a corrugated outer wall of a reversible extension segment.
Figure 4:
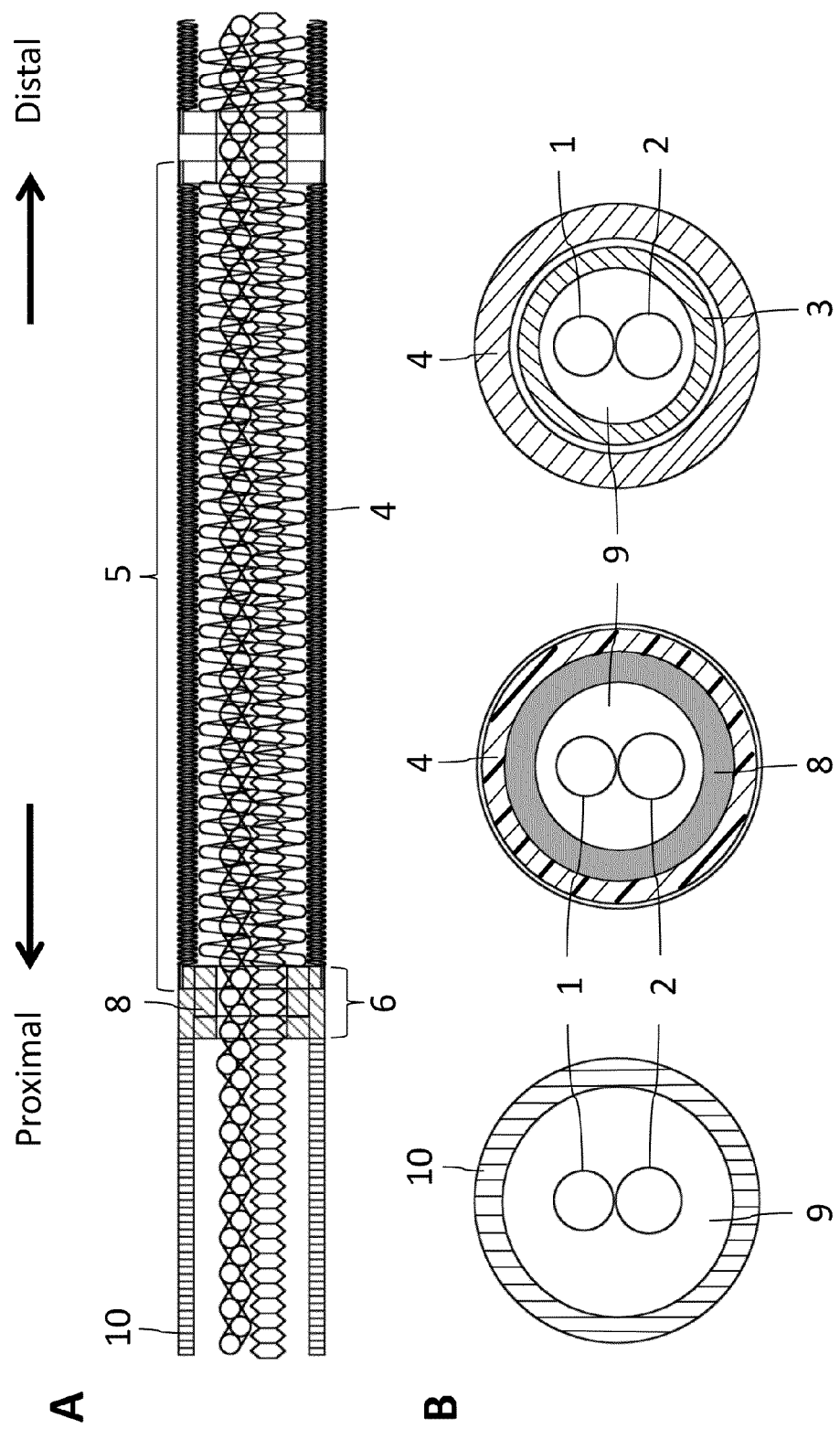
FIG. 4 shows a profile view and cross-sectional views of a single tube-shaped reversible extension segment at a junction with a part of a non-extensible outer wall of a non-extensible tubular shaft.

FIG. 3 shows an exterior look of the outer wall 4 of the reversible extension segment 5. A peak and valley of the circumferential grooves of the corrugated outer wall is configured to have no measurable gap between said circumferential grooves in a neutral, collapsed position.

Referring to the non-extensible tubular shaft D of the overview, FIG. 4A and B show a part of the non-extensible tubular shaft wall 10 attached distally to the junction unit 6. The reversible extension segment 5 is proximally attached to the distal side of said junction unit 6. An increase in volume and pressure of a medium filling the inner tubular space 9 longitudinally extends only the outer wall 4 of the reversible extension segment 5 while the non-extensible tubular shaft wall 10 stays unchanged for its longitudinal length. The longitudinal extension of the reversible extension segment 5 stretches the extension-spring-type coil 3, which in turn generates a recoil of said extension-spring-type coil 3 back toward its neutral position. The extended length of the reversible extension segment 5 results from a balance between the recoil of said extension-spring-type coil 3 and the increase in pressure and volume of the medium in the inner tubular space 9.

Figure 5:
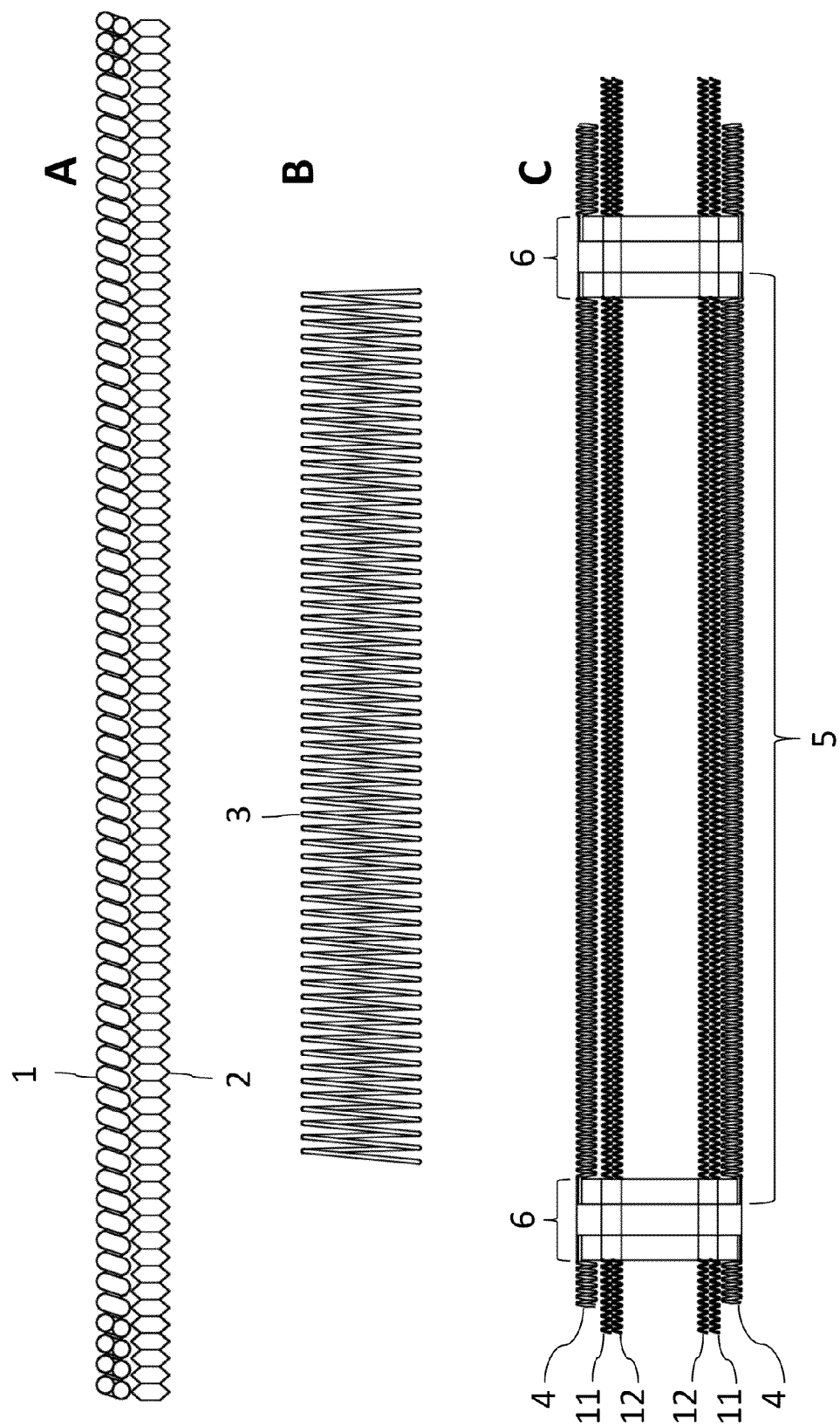
FIG. 5 shows a profile view of itemized components of a concentric cylindrical tube-in-tube reversible extension segment.

Referring to the reversible extensible tubular shaft E of the overview, FIG. 5 depicts individual components of a concentric cylindrical tube-in-tube reversible extension segment in a profile view. FIG. 5A shows both a stretchable spiral-coiled conduit 1 in a coiled configuration with both ends exposing two round outlines of said coiled conduits in each coiled loop and an extensible bellows-shaped channel 2 running in parallel with the stretchable spiral-coiled conduit 1. FIG. 5B shows an extension-spring-type coil 3 that provides circumferential structural rigidity, longitudinal flexibility and recoil upon extension. FIG. 5C shows a single unit of reversible extension segment 5 comprising an outer tubular wall 4, a mid wall 11 and an inner wall 12. Both ends of the reversible extension segment 5 are connected to adjacent reversible extension segments via a junction unit 6. The walls 4, 11 and 12 are configured as circumferentially grooved with corrugation along the longitudinal axis and tightly stacked up in a neutral position, which can be stretched along the longitudinal axis.

Figure 6:
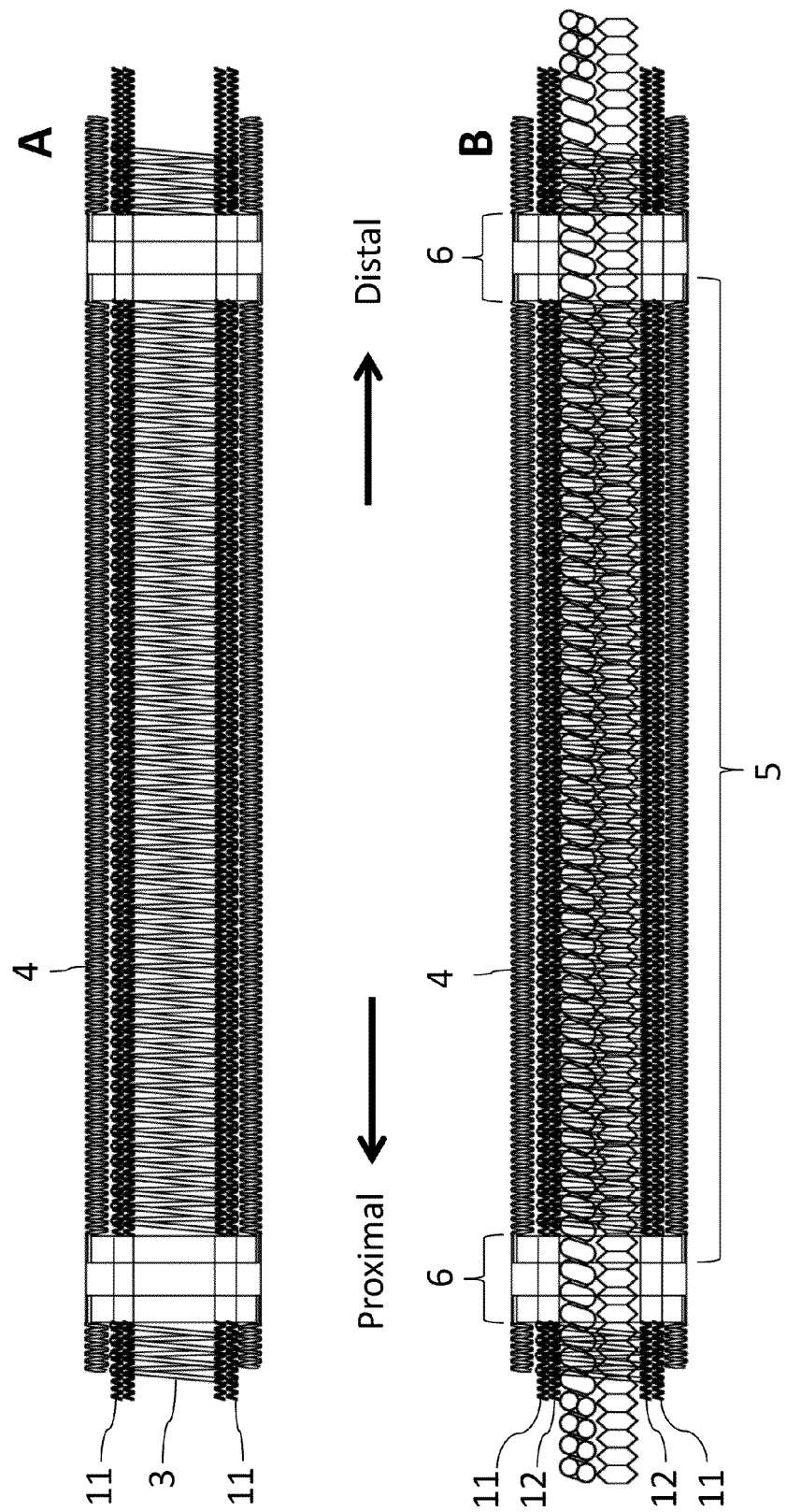
FIG. 6 shows profile views of a concentric cylindrical tube-in-tube reversible extension segment with the itemized components assembled in one piece.

Referring to FIG. 5, FIG. 6 shows a profile view of an assembled reversible extension segment 5. In FIG. 6A, the extension-spring-type coil 3 is longitudinally inserted in between of the stretchable corrugated outer wall 4 and the mid wall 11. FIG. 6B shows a completed assembly of a reversible extension segment 5 with the extension-spring-type coil 3 attached to both proximal and distal sides of the junction unit 6. Both the extensible bellows-shaped channel 2 and the stretchable spiral-coiled conduit 1 run inside the inner wall 12 along the longitudinal axis.

FIG. 7A shows a schematic illustration of an example of sequential extension of a part of a reversible extension segment 5 on both sides of the junction unit 6. The corrugated walls of 4, 11 and 12 become extended tubular walls of 13, 14 and 15, respectively. In between of the extended tubular walls of 13 and 14, there is provided an enlarged outer tubular channel 16. In between of the extended tubular walls of 14 and 15, there is provided an enlarged mid tubular channel 17. An inner tubular space 9 is maintained by the inner wall 15. Upon extension of the reversible extension segment by an increase in pressure and volume of the medium in the inner tubular space 9, an extension-spring-type coil 3 is stretched to become an extended coil 18, a stretchable spiral-coiled conduit 1 becomes an extended spiral-coiled conduit 19 and an extensible bellows-shaped channel 2 becomes an extended bellows-shaped channel 20. A full extension of part of two reversible extension segments joined by the junction unit 6 is depicted in FIG. 7B, showing further longitudinal elongation of both the extended spiral-coiled conduit 19 and the extensible bellows-shaped channel 20.

Figure 7:
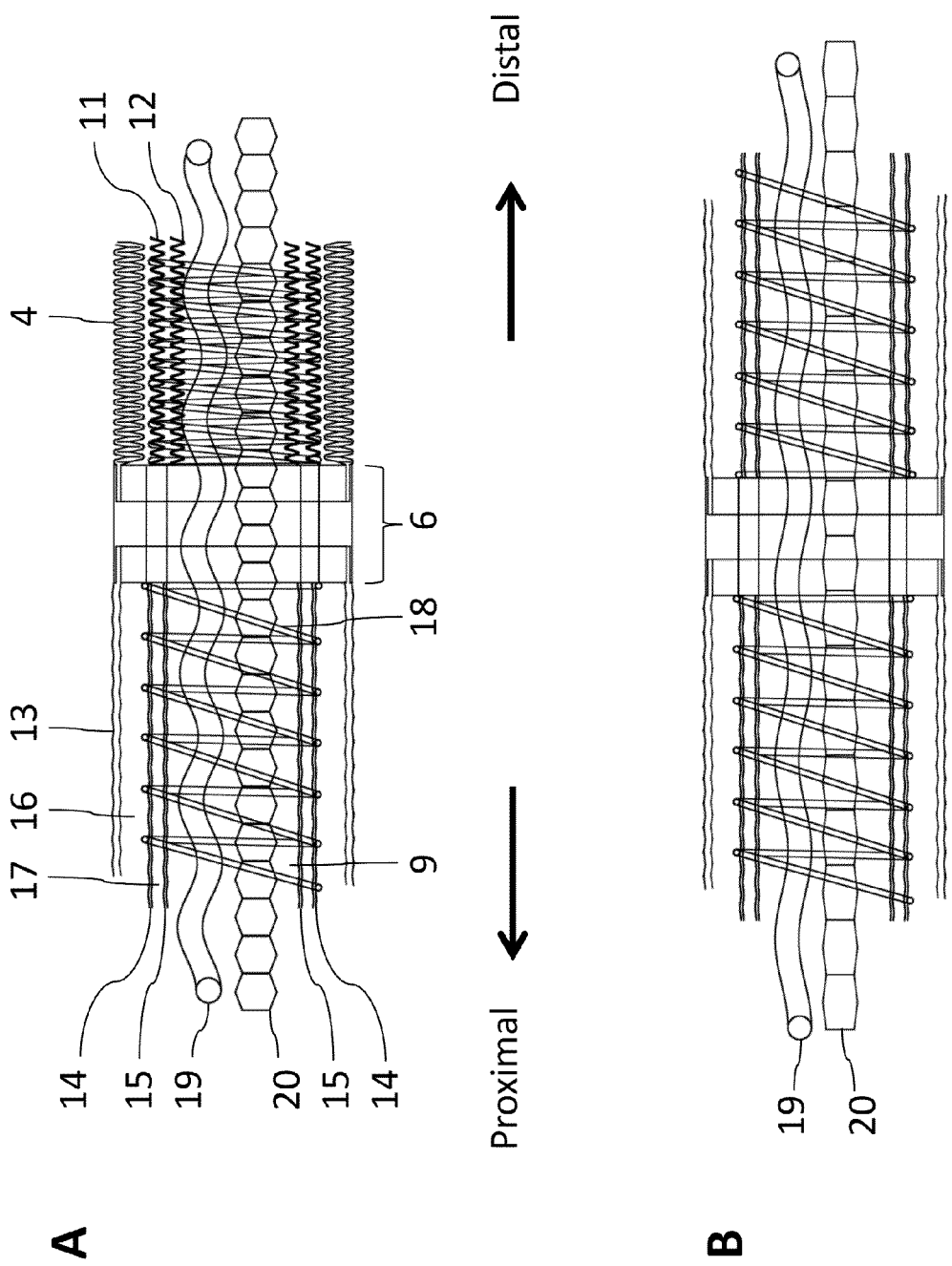
FIG. 7 shows profile views of a part of extension of concentric cylindrical tube-in-tube-shaped reversible extension segments across the junction unit.
Figure 8:
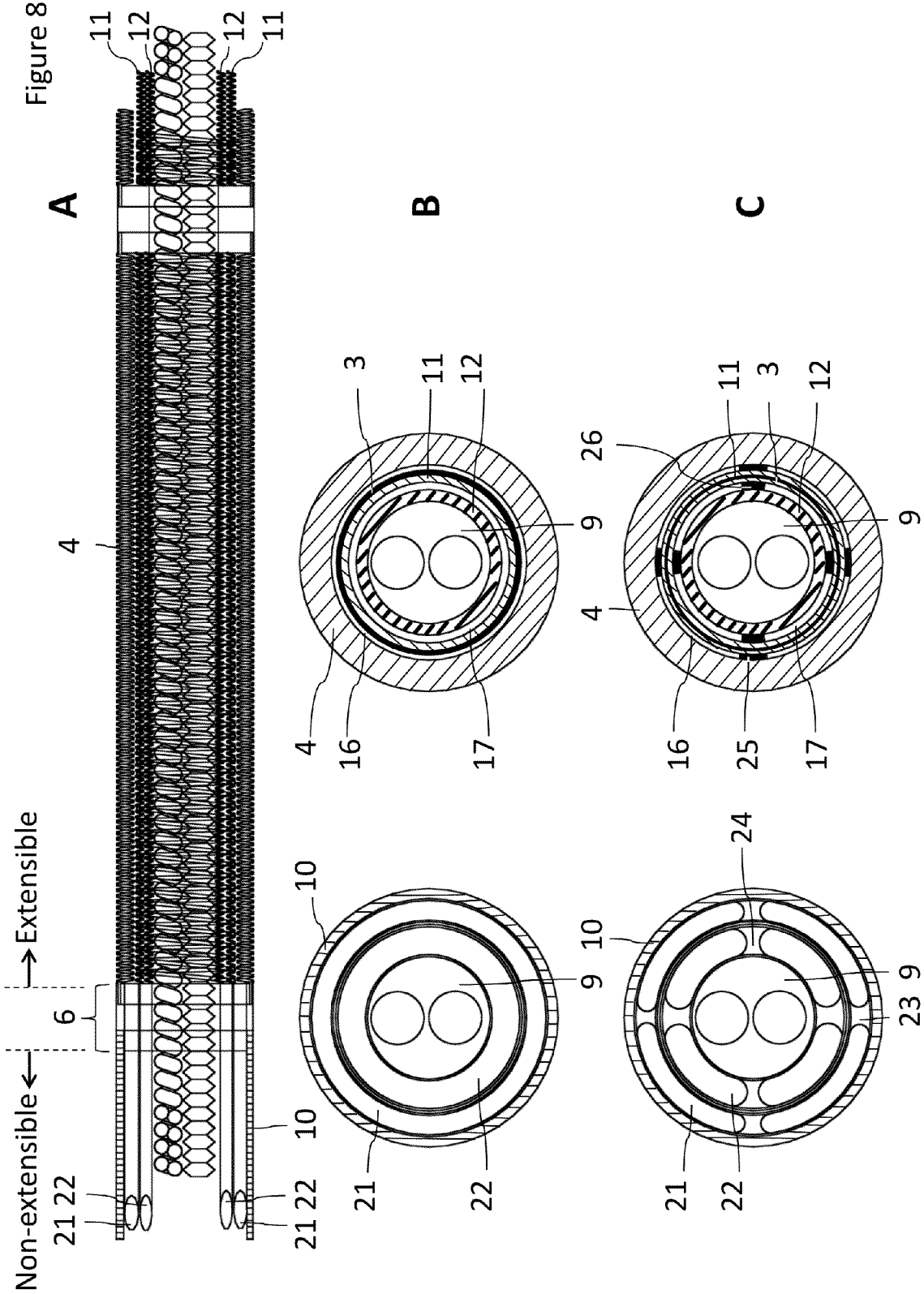
FIG. 8 shows a profile view and cross-sectional views of a concentric cylindrical tube-in-tube reversible extension segment at a junction with a part of the non-extensible tubular shaft.
Figure 9:
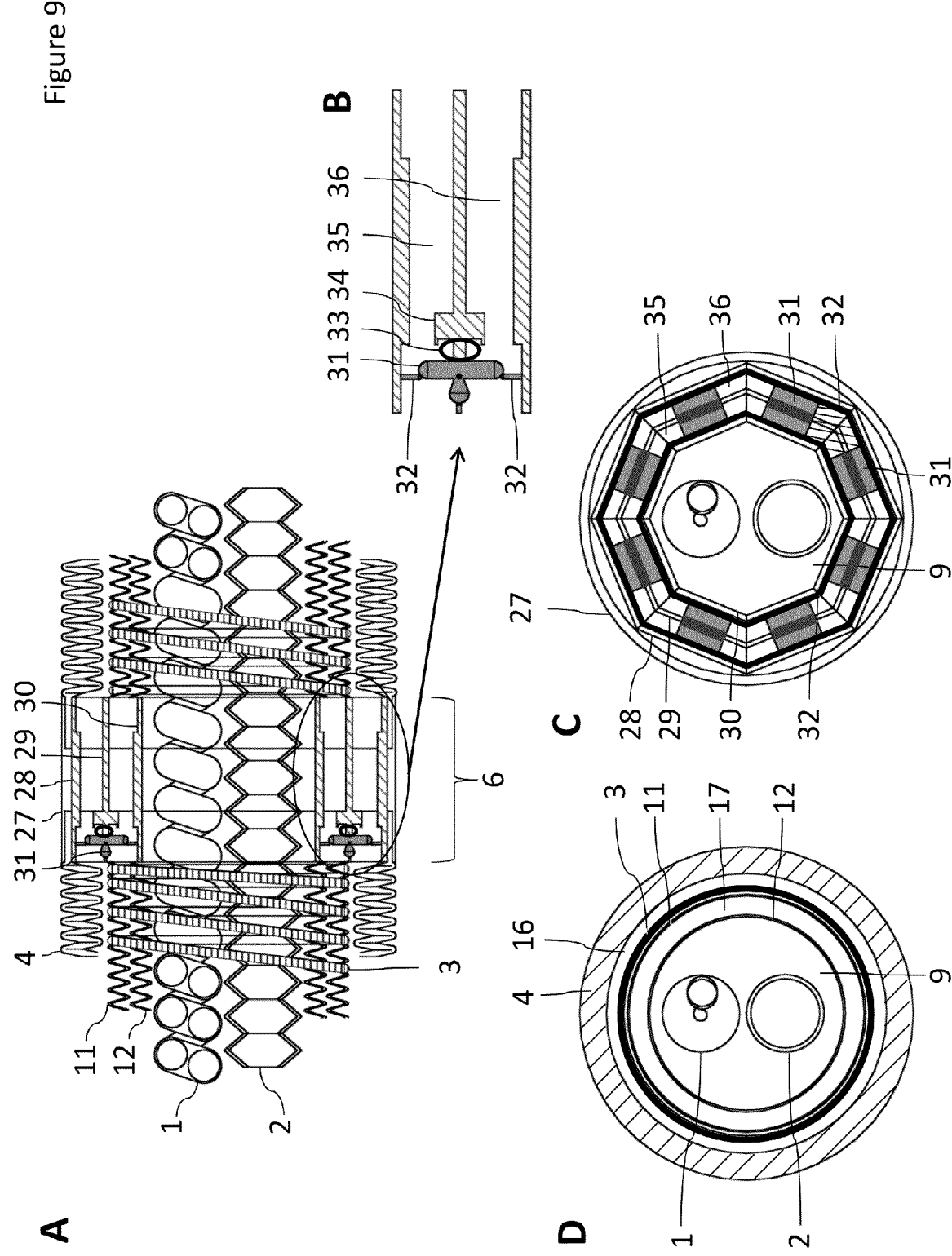
FIG. 9 shows a profile view and cross-sectional views of a junction unit and a part of both ends of reversible extension segments.

FIG. 8A shows a profile view of an example of a distal part of the non-extensible tubular shaft that merges with a reversible extension segment via a junction unit 6. The non-extensible tubular shaft is configured as concentric cylindrical tube-in-tube along the longitudinal axis, comprising a tubular wall 10, an outer cylindrical channel 21, a mid cylindrical channel 22 and an inner tubular space 9. Referring to FIG. 7, an example of a cross-sectional view of the FIG. 8B shows continuation of the outer cylindrical channel 21 to the outer tubular channel 16 and of the mid cylindrical channel 22 to the mid tubular channel 17. The outer tubular channel 16 is bordered by the stretchable corrugated outer tubular wall 4 and the stretchable corrugated mid wall 11. The mid tubular channel 17 is bordered by both stretchable corrugated walls 11 and 12. The extension-spring-type coil 3 circumferentially surrounds the mid wall 11 along the longitudinal axis.

In one embodiment, cylindrical channels of the non-extensible tubular shaft and tubular channels of the reversible extension segments can be divided into a plurality of longitudinally separate channels. FIG. 8C shows a schematic example of a cross-sectional view of the separate channels of both the non-extensible tubular shaft and the reversible extension segment. The outer cylindrical channel 21 and the mid cylindrical channel 22 of the non-extensible tubular shaft are divided into a plurality of longitudinal channels, separated by longitudinal cylindrical gaps 23 and 24, respectively. The outer and mid tubular channels 16 and 17 of the reversible extension segment are divided to a plurality of longitudinal channels, separated by longitudinal cylindrical gaps 25 and 26, respectively. In one embodiment, the stretchable corrugated mid wall 11 is provided as at least two tubular sheets adhered together, in which the extension-spring-type coil 3 is inserted.

FIG. 9A shows a expanded profile view of an example of a junction unit 6 that is attached to both ends of reversible extension segments. For an illustrative purpose, only a part of both ends of reversible extension segments is shown. The junction unit comprises an outer cylindrical tube 27 and a cross-sectionally polygonal chamber that is centrally located inside the outer cylindrical tube. An outer and inner wall of the polygonal chamber are designated as 28 and 30, respectively. The polygonal chamber is longitudinally divided by a chamber divider 29 in the middle of said chamber. At the proximal side of the chamber divider 29, there is provided a T-shaped directional pressure valve 31, with the center of said divider aligned with the longitudinal axis of said chamber divider. FIG. 9B shows an enlarged profile view of an example layout of the polygonal chamber. The T-shaped directional pressure valve 31 is aligned with the center of said polygonal chamber along the longitudinal axis and releasably fastened to said chamber divider 29 via a Belleville-washer-type compression spring 33 and a Belleville-washer-type compression spring holder 34. The polygonal chamber is sealed at the proximal side by a neutral position of the T-shaped directional pressure valve and a valve sealing rim 32 that surrounds said T-shaped directional pressure valve. The T-shaped directional pressure valve is tiltable in the longitudinal direction at center of the T to an outer conduit 35 or an inner conduit 36. Tilting of said directional pressure valve allows opening to either the outer conduit 35 or the inner conduit 36. FIG. 9C shows a cross-sectional view of an example of a proximal side of a junction unit comprising an outer cylindrical tube 27 and an octagonal chamber located inside the outer cylindrical tube. The octagonal chamber is bordered by the outer and inner walls 28 and 30 along the longitudinal axis. The valve sealing rim 32 is located inside both outer and inner walls. The chamber divider 29 divides the chamber into the outer and inner conduits 35 and 36 along the longitudinal axis. For illustration purpose, there is provided a shaded area to indicate that there is no open space in the octagonal chamber between the T-shaped directional pressure valves 31 at the proximal side of the junction unit.

FIG. 9D shows a cross-sectional view of an example of a distal part of a reversible extension segment adjoining the junction unit.

In one embodiment, each set of Belleville-washer-type compression springs for a corresponding junction unit is provided with a predefined range of compressibility that varies for each junction unit. Predefined compressibility of Belleville-washer-type compression springs allows T-shaped directional pressure valves to be tilted upon a certain preset range of pressure of a medium coming to said T-shaped directional pressure valves.

Figure 10:
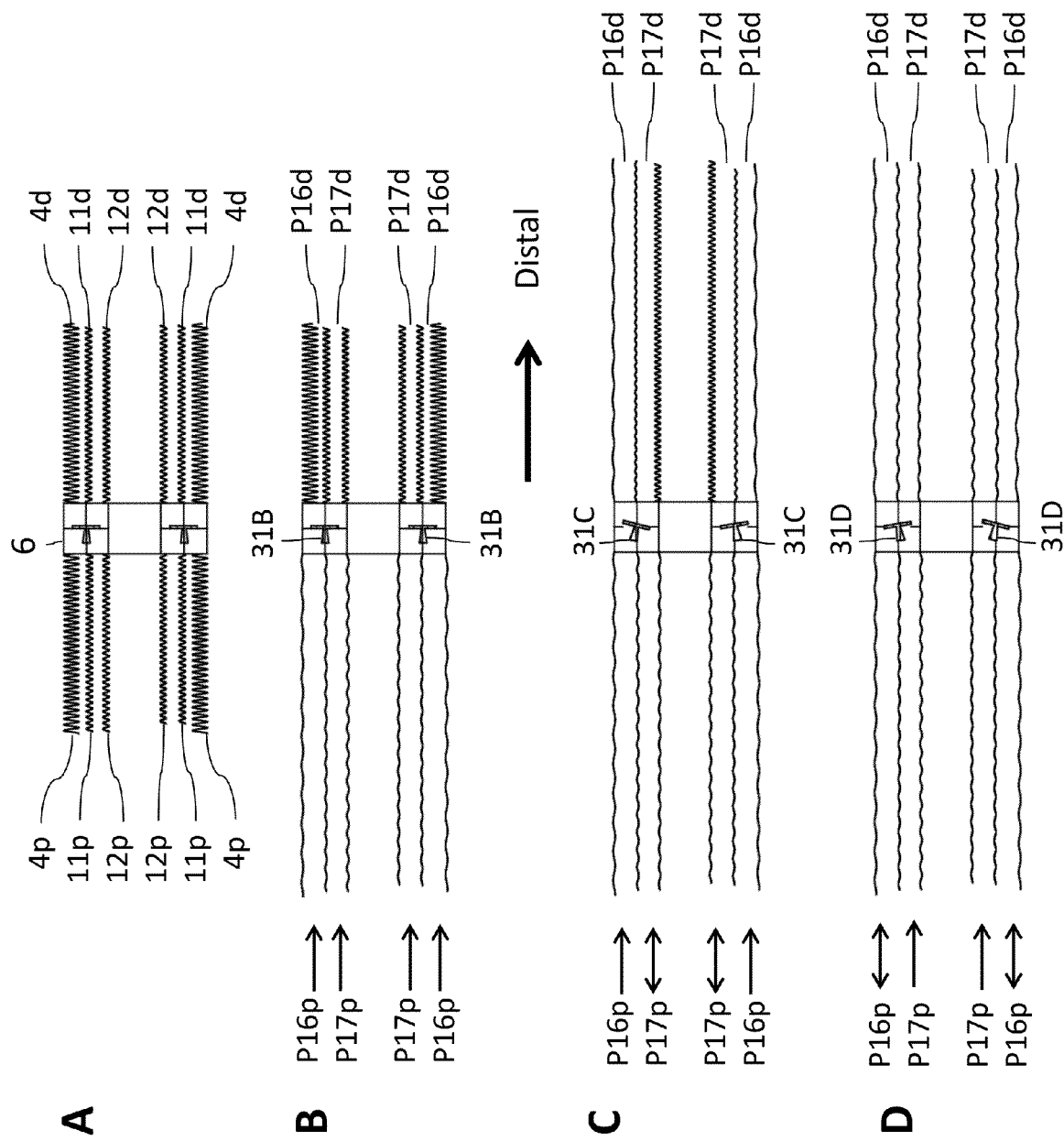
FIG. 10 shows a schematic illustration of sequential extension of tubular walls of concentric cylindrical tube-in-tube-shaped reversible extension segments.

FIG. 10 illustrates a schematic example of principles of sequential extension of reversible extension segments. FIG. 10A represents a neutral, contracted state of part of two reversible extension segments adjoining a junction unit 6. Components of the reversible extension segment located proximal to the junction unit 6 are designated as $4p$ for a stretchable corrugated outer wall; $11p$ for a stretchable corrugated mid wall; $12p$ for a stretchable corrugated inner wall. Similar components of the reversible extension segment located distal to the junction unit 6 are designated with d: $4d$; $11d$; $12d$. FIG. 10B depicts a linear extension of the proximal reversible extension segment along the longitudinal axis while the distal reversible extension segment remains contracted. Said extension of the proximal reversible extension segment is achieved by delivering a medium with an increased pressure of $P16p$ and $P17p$ to both the outer and mid tubular channels, respectively, in which $P16p$ equals $P17p$. An increase in pressure of the medium in said tubular channels increases a volume of the medium in said tubular channels, which then linearly extends the reversible extension segment. The equivalent pressure of both $P16p$ and $P17p$ does not tilt a T-shaped directional pressure valve 31B to either the outer or mid tubular channel of the distal reversible extension segment, thereby maintaining a sealed position of said valve 31B. In this sequence of pressure change of said medium in said tubular channels, equations of individual pressures are as follows: $P16p=P17p$; $P16p>P16d$; $P17p>P17d$; $P16d=P17d$.

FIG. 10C shows an event following a full extension of the proximal reversible extension segment shown in FIG. 10B. In FIG. 10C, the pressure $P16p$ of the medium in the outer channel exceeds the pressure $P17p$ of said medium in the mid channel. Difference in the pressure ($P16p>P17p$) opens the T-shaped directional pressure valve 31C to the outer channel of the distal reversible extension segment, thereby allowing flow of said medium from the proximal outer tubular channel to the distal outer tubular channel across said valve 31C and extending an outer wall of said distal outer tubular channel until both the $P16p$ and $P16d$ become equivalent. In this sequence of pressure changes, equations of said pressure changes are as follows: $P16p>P17p$; $P16p>P16d \rightarrow P16p=P16d$; $P17p>P17d$; $P16d>P17d$.

FIG. 10D shows an additional step of an increase in said pressure $P17p$ of said medium in said mid tubular channel following the extension of the distal outer tubular channel, as illustrated in FIG. 10C. Once said $P17p$ exceeds said $P16p$ in said proximal reversible extension segment, said T-shaped directional valve 31D opens to the distal mid tubular channel. Flow of said medium continues and extends the distal mid tubular channel until the $P17d$ equals the $P17p$. In this sequence of pressure changes, equations of said pressure changes are as follows: $P16p<P17p \rightarrow P16p=P17d$; $P16p=P16d$; $P17p>P17d \rightarrow P17p=P17d$; $P16d>P17d \rightarrow P16d=P17d$.

FIG. 11 shows a numerical example of different pressures of a medium in said respective tubular channels across said T-shaped valves of 31B, 31C and 31D, as described in FIG. 10. Referring to FIG. 9B, a range of pressure changes required to tilt and open T-shaped directional pressure valves to tubular channels can be preset by a range of compressibility of the Belleville-washer-type compression springs.

Referring to FIG. 8C, FIG. 12 shows a numerical example of different pressures of a medium in tubular channels for sequential extension and bending of reversible extension segments. The present example has four tubular channels inside three reversible extension segments arranged in tandem, which can be extended and bent by differential lengthening of individual channels. Said tubular channels are extended individually by an increase in pressure and volume of the medium in each said tubular channel. Differences in pressure and volume of the medium among said tubular channels result in length differences of individual tubular channels of a reversible extension segment. In this example, only the pressure changes are described solely for a purpose of mechanistic explanation and should be regarded as equivalent to changes in volume of a medium. In the table, OP stands for outer tubular channel pressure and MP for mid tubular channel pressure. Row A represents an example of different pressures in tubular channels for extension and bending of the first reversible extension segment. A linear extension of said reversible extension segment requires equal pressures in all four tubular channels. An example of said pressure resulting in a full extension of the reversible extension segment is represented in the table as 50. A pressure 48 in up to three tubular channels, compared to said pressure 50 in other tubular channel(s), is associated with a shorter length of the tubular channel(s). Said pressure difference of the medium causes bending of said reversible extension segment.

As described in Row B of FIG. 12, for the first reversible extension segment following the extension and/or bending, pressure differences between the outer tubular channel pressure and the mid tubular channel pressure can be induced to tilt and open T-shaped directional pressure valves of a junction unit to corresponding tubular channels of the second reversible extension segment that is distally located to the first reversible extension segment. Subsequent to insufflation of the medium to said tubular channels and extension of the second reversible extension segment, both outer and mid tubular channel pressures can be equalized over a range of preset pressure for linear extension of said second reversible extension segment, exemplified in Row C. The sequence of 'extension and/or bending of a reversible extension segment, followed by venting of a medium to the next reversible extension segment and by pressure equalization' can be repeated as illustrated in Rows D, E and F, over the entire extension shaft until said extension shaft is fully extended and/or bent to a target area.

Figure 13:
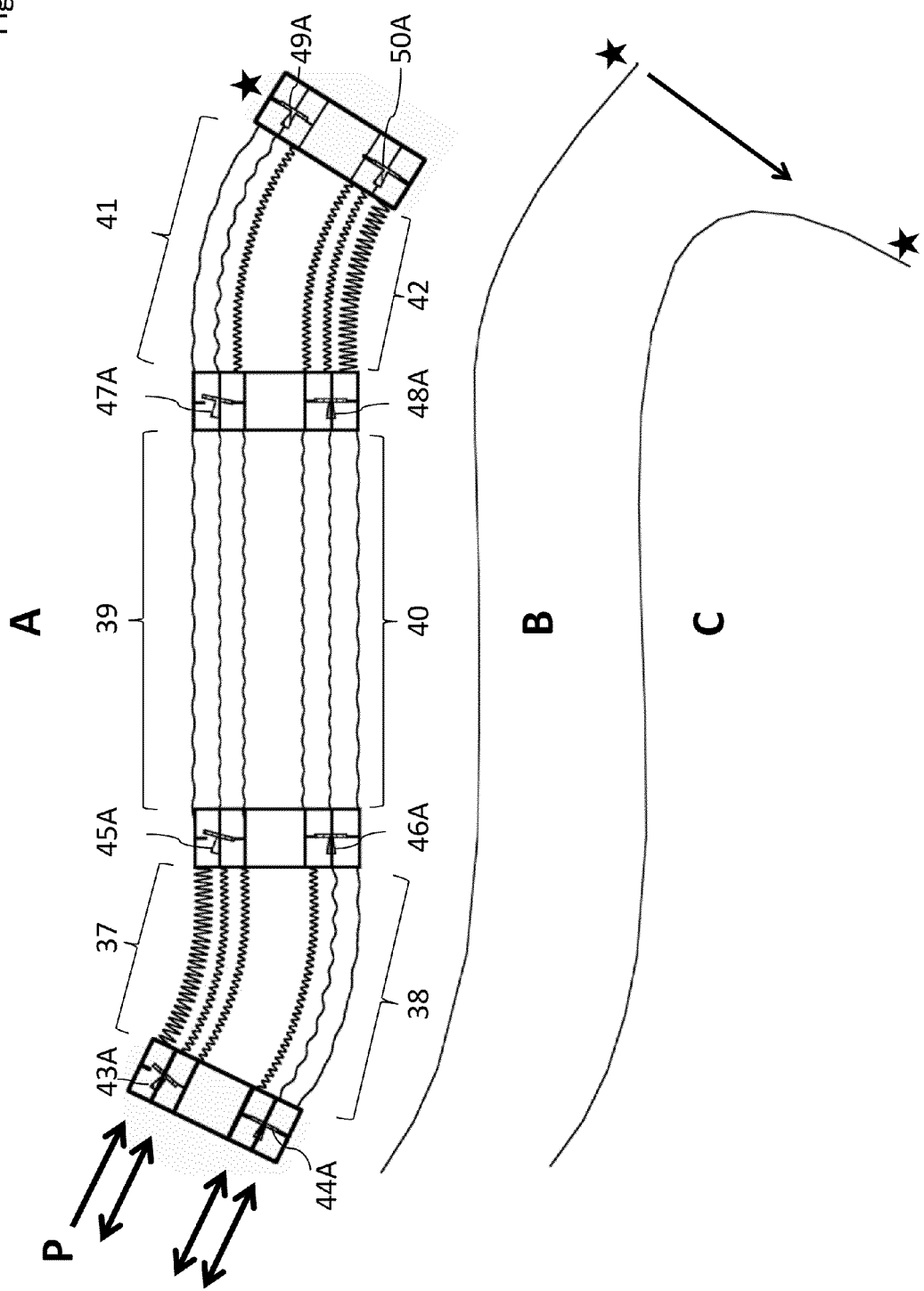
FIG. 13 illustrates an example of bending of concentric cylindrical tube-in-tube reversible extension segments by pressure changes.
Figure 14:
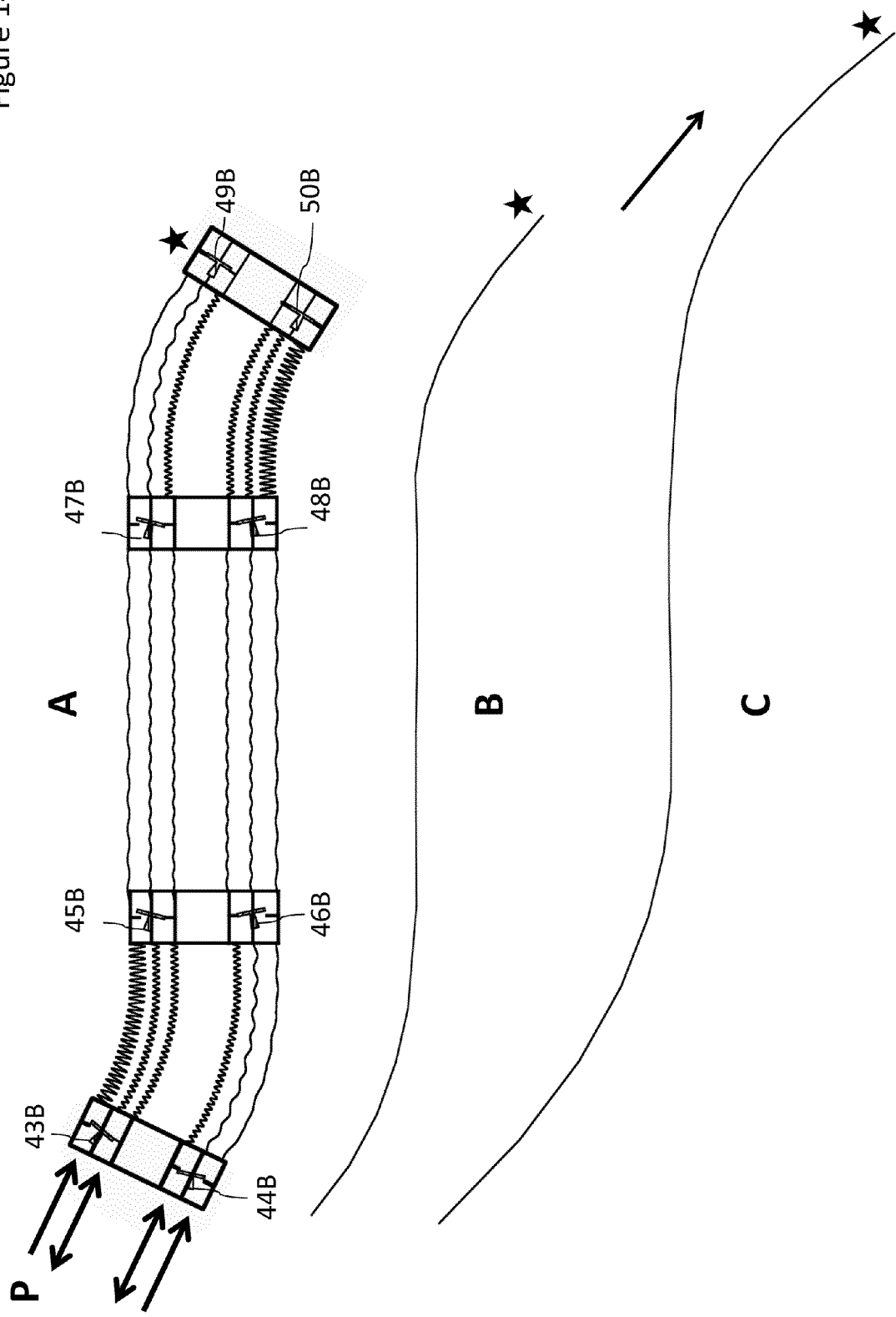
FIG. 14 illustrates an example of a forward advancement of concentric cylindrical tube-in-tube reversible extension segments by pressure changes.

FIG. 13 shows a schematic example of a bending of a reversible extension segment, according to the description of FIG. 12. In FIG. 13A, there are three reversible extension segments represented as '37-38', '39-40' and '41-42'. T-shaped directional pressure valves of junction units are designated as 43A to 50A. P stands for pressure of a medium coming to tubular channels. T-shaped directional pressure valves 43A, 45A and 47A are in an open position upon an increase in pressure to an outer tubular channel bordered by a stretchable corrugated outer wall 37, while the other tubular channels maintain an unchanging pressure. T-shaped directional pressure valves 43A-50A have a preset compressibility that needs to be overcome by increases in pressure of the medium in said tubular channels, to be tilted to an open position. In FIG. 13A, the increase in the pressure coming to the valve 49A does not overcome the compressibility of the valve 49A. Consequent to the increase in the pressure only in one outer tubular channel bordered by a stretchable corrugated outer wall 41, the reversible extension segment '41-42' bends to a direction of the valve 50A, as schematically illustrated in FIGS. 13B and 13C.

FIG. 14A shows a schematic example of a linear extension of reversible extension segments by an increase in pressure of a medium in two opposite outer tubular channels. As in FIG. 13A, the increase in the pressure of the two opposite tubular channels does not overcome the compressibility of valves 49B and 50B, but can tilt valves 43B-48B to an open position to corresponding tubular channels. The reversible extension segments extend while maintaining the bent configuration, as illustrated in FIGS. 14B and 14C. Further increase in the pressure beyond the compressibility of the valves 49B and 50B to extend subsequent reversible extension segments may not change the bent configuration as long as there is no change in the pressure differences among the first to fourth tubular channels, as described in FIG. 12.

Figure 15:
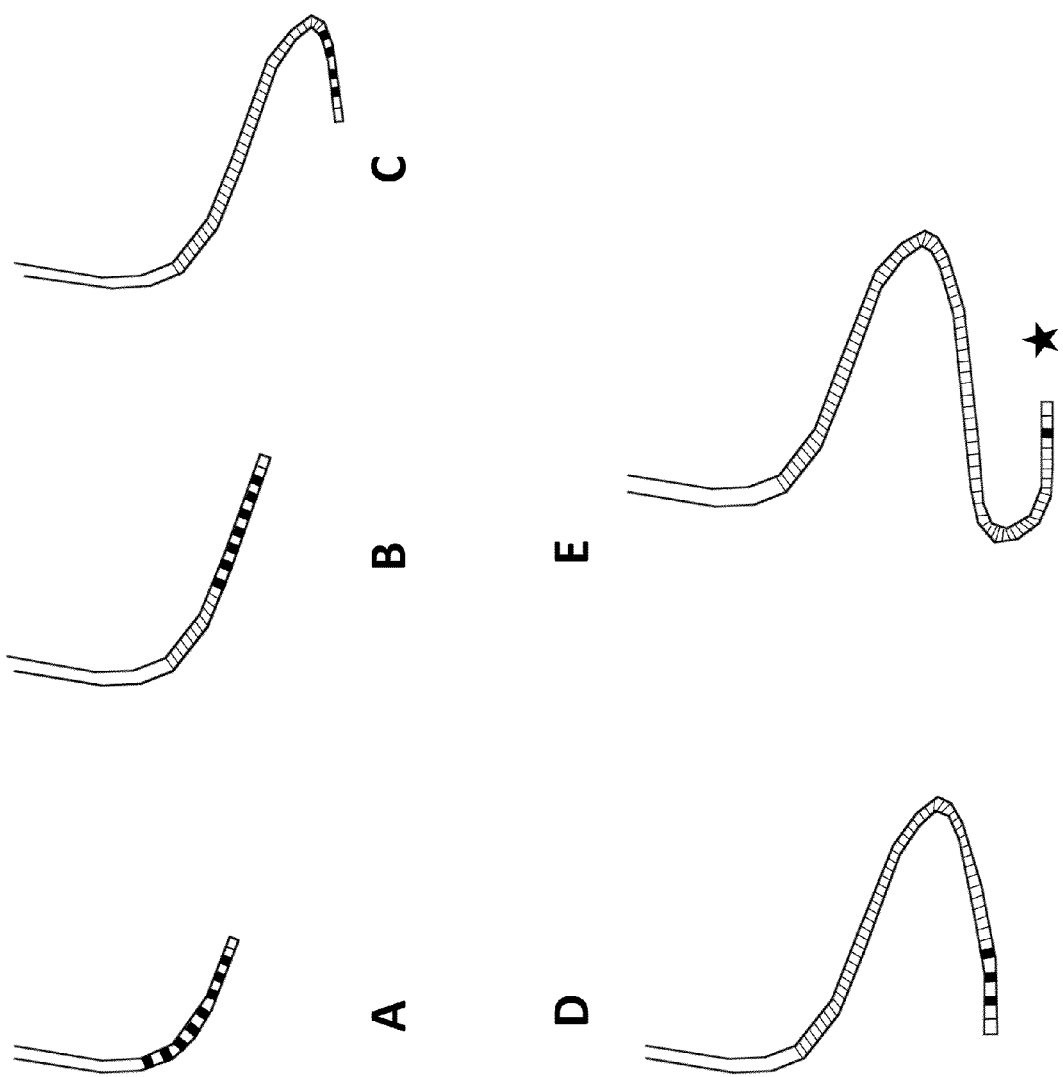
FIG. 15 shows a schematic overview of sequential forward extension of the reversibly extensible tubular shaft.

FIG. 15 depicts a schematic example of a sequence of extension and bending of an extension shaft of a flexible tubular device. A neutral, contracted state of the extension shaft is shown in FIG. 15A. Said extension shaft begins to extend distally from the proximal part of said shaft, by extension of individual reversible extension segments, as illustrated in FIG. 15B. Said extension shaft bends at one reversible extension segment to one direction and linearly extends further distally, as shown in FIGS. 15C and 15D, respectively. Another bending at a different reversible extension segment to a different direction from the prior bending followed by linear extension occurs to reach a target area, as shown in FIG. 15D.

Figure 16:
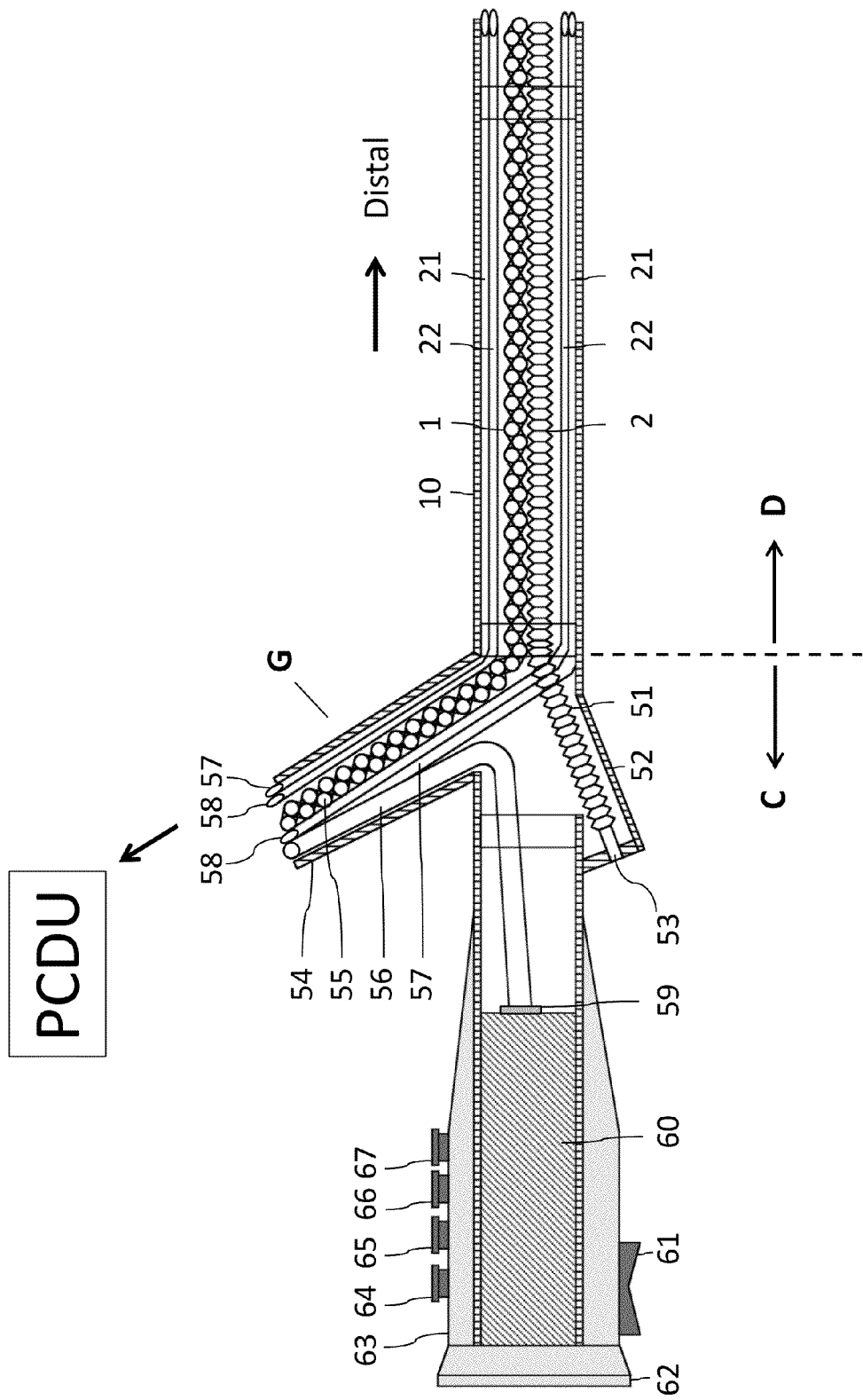
FIG. 16 shows a profile view of a proximal end of the tubular device with a part of a connecting tubular shaft to the PCD unit and a part of the non-extensible tubular shaft.

FIG. 16 shows a profile view of a proximal end of the tubular device with a part of a connecting tubular shaft G to the PCD (Power, Control & Display) unit and a part of the non-extensible tubular shaft. Referring to C and D of FIG. 1, the non-extensible shaft D is configured as a flexible, longitudinally cylindrical tube comprising the non-extensible outer wall 10, the outer and mid cylindrical channels 21 and 22 circumferentially disposed inside the non-extensible outer wall 10, the stretchable spiral-coiled conduit 1 and the extensible bellows-shaped channel 2, with both 1 and 2 running longitudinally in the inner tubular space 9. The stretchable spiral-coiled conduit 1 becomes a stretchable spiral-coiled conduit 55 in the connecting tubular shaft G and is connected proximally to the PCD unit for gas, water, electricity and negative suctioning. The stretchable spiral-coiled conduit delivers electricity, gas and water to the distal end of the tubular device, produces light to illuminate an area under examination and suctions out materials from the area under examination. One important function of the stretchable spiral-coiled conduit is to directionally bend the distal end, which is separately controllable from the extension and bending of the extension shaft of said device. The extensible bellows-shaped channel 2 serves as conduit for instruments including tissue biopsy forceps and for delivering agents such as drugs or water to an area of examination.

Both the outer and mid cylindrical channels 21 and 22 of the non-extensible shaft D become an outer tubular conduit 57 and a mid tubular conduit 58 in the connecting tubular shaft G, respectively, to get connected to the PCD unit for a filling medium under pressure. The conduits 57 and 58 and the cylindrical channels 21 and 22 deliver the medium to the reversible extension segments of the extension shaft and mediate pressure changes generated by the PCD unit. The connecting tubular shaft G is configured as cylindrically tubular and comprises a flexible, non tubular wall 54 and connects the proximal end C to the PCD unit. Referring to FIG. 1, the stretchable spiral-coiled conduit 1 is maintained as coiled in both the non-extensible shaft D and connecting tubular shaft G in a neutral, contracted state of the extension shaft E. Said spiral-coiled conduit 1 uncoils and longitudinally stretches upon extension of the extension shaft E. The extensible bellows-shaped channel 2 is connected to a hub 53 located on a side of the proximal end via a junctional part 51 of the extensible bellows-shaped channel. The junctional part 51 of the extensible bellows-shaped channel runs at an obtuse angle to the longitudinal axis of the tubular shaft inside a housing 52 that is a part of the proximal end of said tubular shaft. The extensible bellows-shaped channel 2 is maintained as collapsed from the hub 53 to a junction with a distal end along the longitudinal axis of the tubular shaft in a neutral, contracted state of the extension shaft E. Said extensible bellows-shaped channel 2 longitudinally stretches upon extension of the extension shaft E.

The proximal end C is configured for hand-held operation of the tubular device and comprises a control knob 61 for directional bending of the distal end, an electronic display unit of visual information 62, a proximal end housing 63, a control knob 64 for extension and bending of the extension tubular shaft, control knobs 65 and 66 for water and gas, respectively, and a control knob 67 for suctioning. An electronic control module 60 of said proximal end is located inside the proximal end housing 63 and is connected to the PCD unit via a bundle 56 of electric cables that run inside the connecting tubular shaft G. The electric cable bundle 56 is attached to the electronic control module 60 via a connection hub 59. Said control knobs of the proximal end allow the tubular device to reach a target area, to insufflate gas, to administer water, to suction materials out and to electronically communicate with the PCD unit for additional function of the tubular device.

Figure 17:
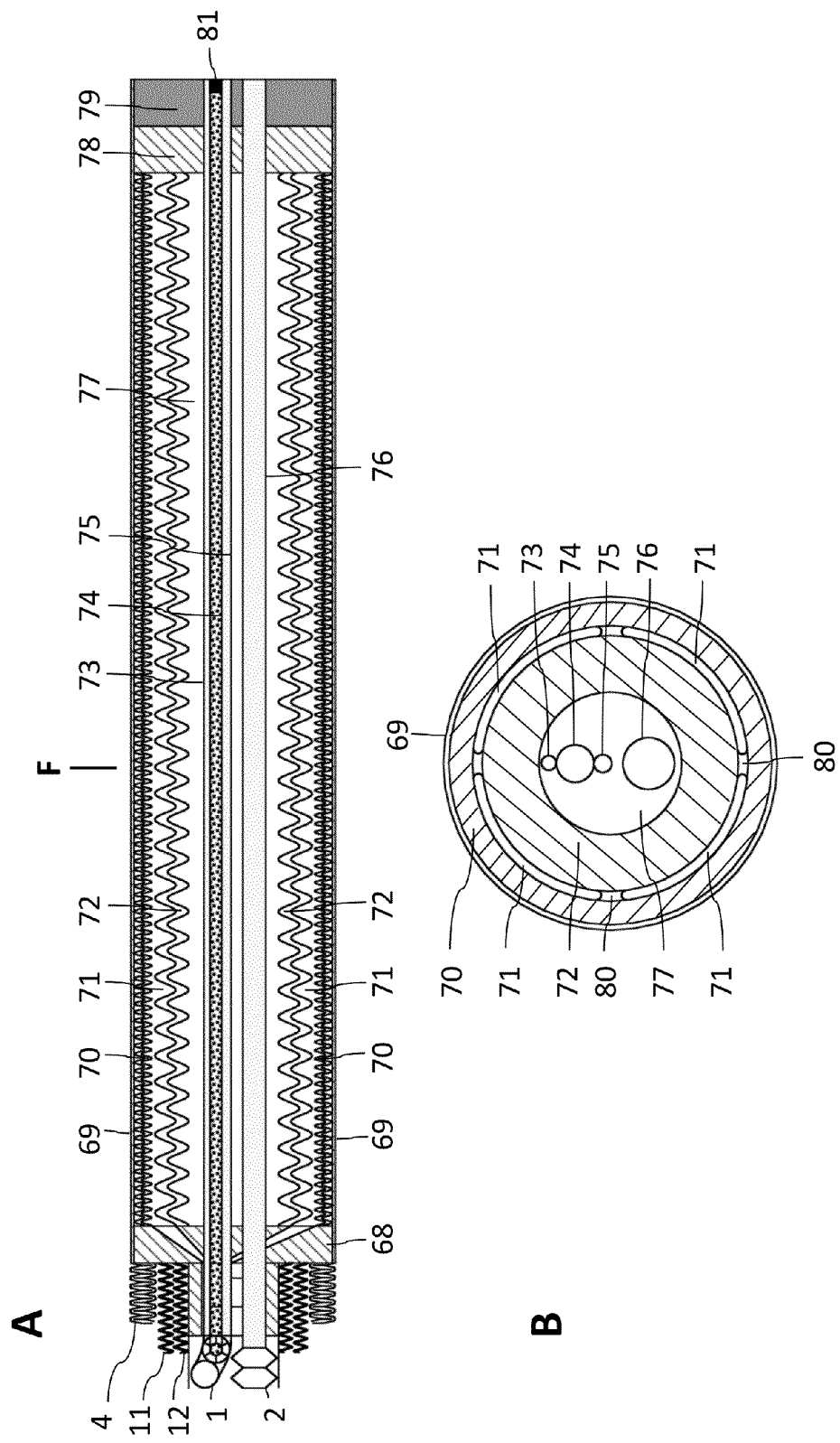
FIG. 17 shows a profile view and a cross-sectional view of a distal end with a distal end joint and a part of a reversible extension segment attached to the distal end joint.

FIG. 17 A and B show a profile view and a cross-sectional view of the distal end F proximally adjoining a distal end joint 68, respectively. A distal part of a reversible extension segment is shown attached to the distal end joint F. Part of the non-collapsible stretchable spiral-coiled conduit 1 located immediately proximal to the distal end joint 68 uncoils to become straightened electric cables 74 for an image acquisition complex 81 comprising a CCD image sensor complex and a plurality of LED located at the most distal end and for a solenoid assembly 78, a straightened water channel 73 and gas channel 75. Said wires 74, said water and gas channels 73 and 75 run longitudinally from the distal end joint 68 in an inner air chamber 77 through the solenoid assembly 78 and a distal end cap 79 to the most distal end. The electric cables 74 provide electricity to the LED for light illumination of a target area and transmit electronic information generated by the CCD image sensor complex to the PCD unit and to the electronic display unit 62 at the proximal end. Both the water and gas channels 73 and 75 run in parallel with the electric cables 74 and open to the most distal end in close proximity to the CCD image sensor complex 81. The water channel 73 cleanses an exposed end of the image acquisition complex 81 and the gas channel 75 brings in gas that may include ambient air from the PCD unit to an area of examination.

Another part of the stretchable spiral-coiled conduit 1 uncoils to get connected in the distal end joint 68 to a plurality of collapsible corrugated outer pressure chambers 71 of the distal end F. The pressure chambers 71 may be filled with a medium of gas such as $CO_2$ or ambient air or of liquid including gaseous phase of liquid. The corrugated outer pressure chamber 71 is surrounded by a non-elastomeric collapsible corrugated mid wall 70 on the outside and by a non-elastomeric collapsible corrugated inner wall 72 on the inside and is configured to shrink longitudinally along the axis. Both the collapsible corrugated mid and inner wall 70 and 72 are configured as concentric cylindrical tube-in-tube along the longitudinal axis of the distal end F, connected proximally to the distal end joint 68 and distally to the complex of the solenoid assembly 78 and the distal end cap 79. The collapsible corrugated mid wall 70 is circumferentially surrounded by and irreversibly glued to a non-elastomeric outer wall 69 of the distal end F. A plurality of the outer pressure chambers 71 are evenly separated from each said chamber by a longitudinally cylindrical gap 80 along the longitudinal axis of the distal end. The non-collapsible stretchable spiral-coiled conduit 1 has a plurality of conduits corresponding to the number of the outer pressure chambers, with each conduit connected distally to each collapsible outer pressure chamber and proximally to the PCD unit in a way each conduit is connected to a negative suctioning device located in the PCD unit. Negative suctioning of the medium from one or a plurality of the collapsible outer pressure chambers collapses said outer chambers, resulting in shortening of a longitudinal length of said outer chambers. Differential shortening of the longitudinal length of said outer chambers produces bending of the distal end.

The extensible bellows-shaped channel 2 gets straightened at the distal end junction and is connected to a tubular channel 76 that runs through both the solenoid assembly 78 and distal end cap 79 to open to the end of the distal end F. The distal end cap 79 fastens in place the image acquisition complex 81 connected to the electric cables 74, the water channel 73, the gas channel 75 and the tubular channel 76. In addition, the distal end cap 79 fastens together the outer wall 69, the collapsible corrugated mid and inner wall 70 and 72 for air-tight sealing. In one embodiment, the solenoid assembly 78 is configured to generate static electromagnetic field by direct electric current with North and South poles on each side of said solenoid assembly, respectively, along the longitudinal axis. Reversible on-off generation of the electromagnetic field is to reversibly push and retrieve corresponding magnetic metallic instruments releasably inserted in the extensible bellows-shape conduit to the distal end cap. The solenoid assembly is connected to the PCD unit via electric cables 74 of the stretchable spiral-coiled conduit 1.

Figure 18:
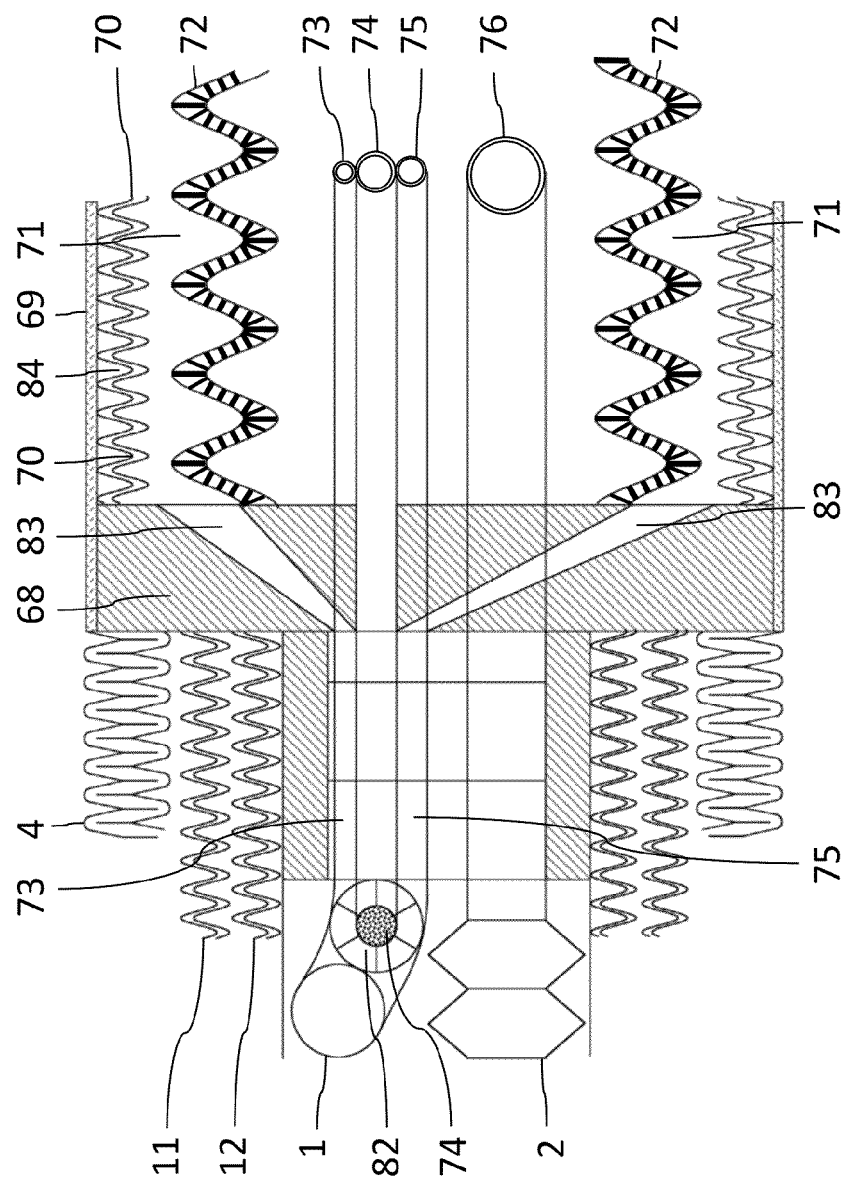
FIG. 18 shows a profile view of a distal end joint and of a part of a reversible extension segment and of a part of the distal end.

FIG. 18 shows an enlarged profile view the distal end joint 68 and a part of a reversible extension segment and of the distal end adjoining both sides of the distal end joint. The stretchable spiral-coiled conduit 1 is configured as concentrically honeycomb on cross-section at a right angle to the longitudinal axis, as illustrated as 82. The concentric honeycomb conduit 82 comprises the electric cables 74 in the center of said honeycomb conduit. The water and gas channels 73 and 75 and conduits for negative suctioning of the collapsible outer pressure chamber 71 are located concentrically around the electric cables 74 in honeycomb configuration. The distal end junction 68 is configured for air-tight seal between said distal end junction and the distal end cap 79, except that said junction 68 is perforated obtusely along the longitudinal axis by tunnels 83 connecting the conduits of the stretchable spiral-coiled conduit 1 for negative suctioning to the collapsible outer pressure chambers 71 and perforated at a right angle to the longitudinal axis for the electric cables 74, the water and gas channels 73 and 75 and the tubular channel 76 proximally connected to the extensible bellows-shaped channel 2. Between the outer wall 69 of the distal end and the collapsible corrugated mid wall 70, there is provided a dead space 84 that is configured to accommodate passive longitudinal shortening of the corrugated mid wall 70 on negative suctioning on the collapsible outer pressure chamber 71.

Figure 19:
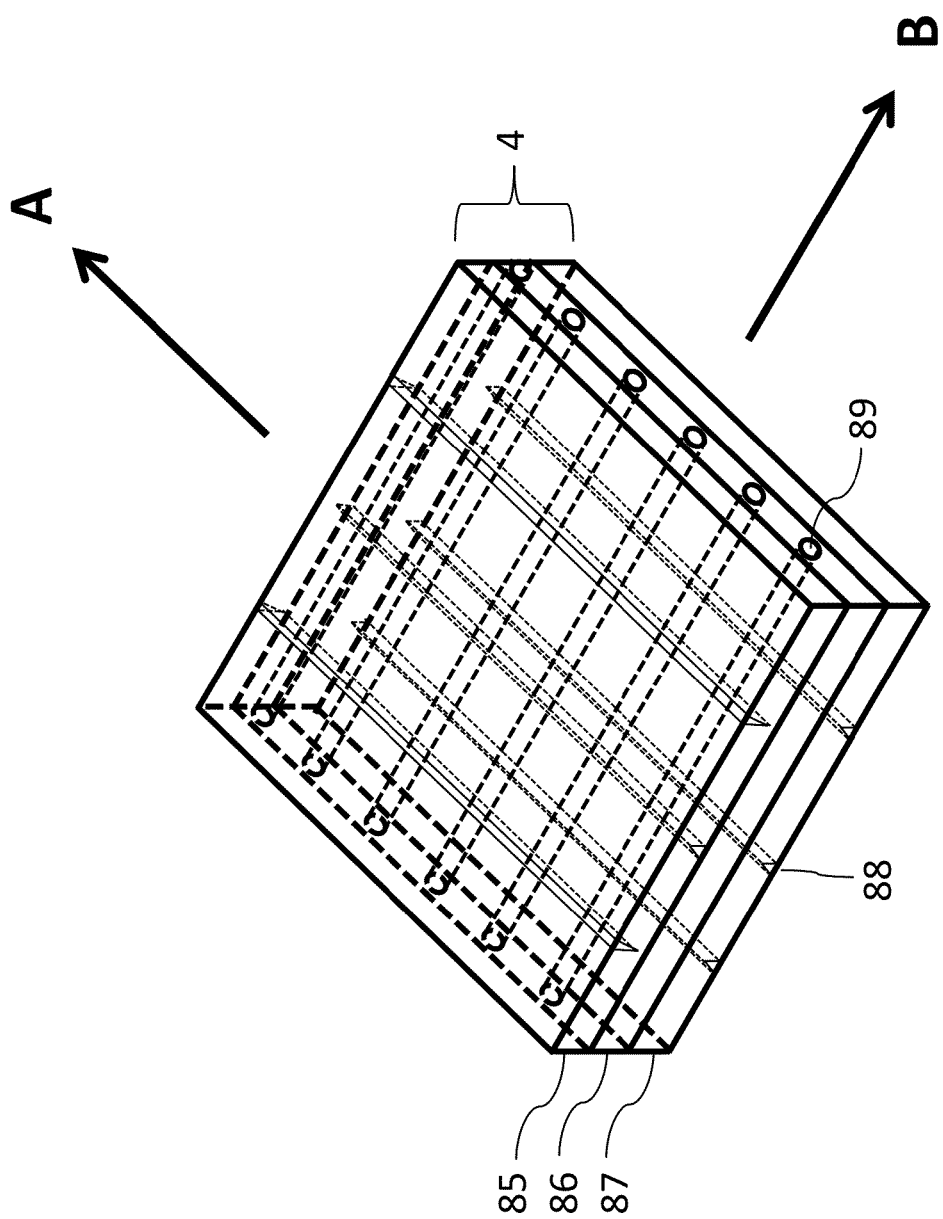
FIG. 19 shows an example of a three dimensional view of a rectangular piece of an outer wall of a reversible extension segment.

FIG. 19 shows an illustrative example of a three dimensional view of a rectangular piece of a tubular wall of a reversible extension segment. A full thickness of the wall 4 is configured to withstand multiple shortening and extension without wear and tear, to fold without resistance along circumferentially corrugated grooves and to maintain tensile strength as a tubular wall of the tubular shaft. In the illustrated example, said wall comprises three thin polymer sheets adhered together, with each sheet having a different tensile direction for axial stretch. In one embodiment, a top sheet 85 and a bottom sheet 87 have a tensile direction to A whereas a middle sheet 86 has a tensile direction to B, with both A and B directions being at a right angle to each other. The longitudinal axis of the tubular device is provided as B. Both the top and bottom sheets 85 and 87 have circumferentially notched grooves 88 that are aligned together. The grooves of the top sheet are notched on the outer surface of said top sheet and the grooves of the bottom sheet are notched on the inner surface of said bottom sheet. The outer wall 4 gets folded and extended at said grooves. The middle sheet 86 is embedded with multiple linear reinforcement polymer strings 89 along the longitudinal axis and is configured to maintain a tubular shape of the tubular shaft over a long distance of said tubular shaft without unintended bending or narrow angulation along the longitudinal axis of the tubular shaft due to a heavy weight of said tubular shaft over the long distance from the proximal end to the distal end of the tubular device.

A terminology for the present apparatus is defined as 'prolixoscope', indicating that the apparatus extends in space and has functionality of endoscope.

It is to be understood that the aforementioned description of the apparatus and methods is simple illustrative embodiments of the principles of the present invention. Various modifications and variations of the description of the present invention are expected to occur to those skilled in the art without departing from the spirit and scope of the present invention. Therefore the present invention is to be defined not by the aforementioned description but instead by the spirit and scope of the following claims.

What is claimed is:

1. An extensible and guidable endoscopic apparatus comprising: an extensive and guidable pressure-sealed endoscopic flexible tubular device, having a proximal end, a distal end, a flexible tubular shaft connecting said proximal and distal ends, a plurality of extension-spring-type coils, a stretchable conduit, a plurality of extensible channels and a medium of gas or liquid filling said endoscopic flexible tubular device, which is configured to be inserted into a lumen or a cavity of a living body to reach a target area the proximal end, provided in a mechanical and electrical configuration, connected to both said flexible tubular shaft and a power, control and display (PCD) unit, which controls said endoscopic flexible tubular device for longitudinal extension and shortening of said flexible tubular shaft, for pressure mediated bending of said distal end, for delivery of and suctioning of materials to and from said target area, for acquisition and display of visual information and for instrumentation to said target area; the distal end, provided in a mechanical and electrical configuration, having a distal portion of said stretchable conduit, a distal portion of a plurality of said extensible channels, a plurality of non-elastomeric collapsible concentric cylindrical tube-in-tube pressure chambers, a distal end joint, a distal end cap with a solenoid assembly, an image sensor and a light source connected to electric cables, which provides pressure-mediated controllable bending of said distal end, delivery and suctioning of materials to and from the target area, acquisition of visual information and instrumentation to said target area; the flexible tubular shaft, provided in a mechanical configuration, having a non-extensible tubular shaft connected distally and longitudinally in tandem to a reversibly extensible tubular shaft comprising a plurality of reversible extension segments, which provides controllable longitudinal extension and shortening and bending of said reversible extensible tubular shaft; the extension-spring-type coil longitudinally placed inside each reversible extension segment, which provides said reversible extension segment with circumferential structural rigidity, longitudinal flexibility and recoil upon extension; the stretchable conduit comprising electric cables, gas and water channels and pressure conduits, configured in a spiral coil longitudinally and in a concentric honeycomb circumferentially, which runs longitudinally from the PCD unit to the distal end and is longitudinally stretchable, and which delivers gas, water, negative suctioning and electricity to said distal end; the extensible channels, configured in a cylindrically tubular bellows, which runs from the proximal end to the distal end and are longitudinally extensible, and which serve as conduit for longitudinally linear instruments and for delivering materials to the target area; the medium, provided as one or a mixture of gas or of liquid including a gaseous phase of liquid, which fills the entire pressure-sealed internal space of said endoscopic flexible tubular device and is controlled for pressure and volume of said medium by the PCD unit, and which provides said endoscopic flexible tubular device with extension, shortening and bending;

a plurality of the collapsible concentric cylindrical tube-in-tube pressure chambers of the distal end made of a plurality of non-elastomeric corrugated tubular walls, which is connected proximally to the distal end joint and distally to the complex of the solenoid assembly and the distal end cap;

the collapsible concentric cylindrical tube-in-tube pressure chambers of the distal end are longitudinally and evenly separated from each said chamber by a longitudinal cylindrical gap along the longitudinal axis of the distal end from the distal end joint to the distal end cap;

each said collapsible concentric cylindrical tube-in-tube pressure chamber of the distal end is connected to a conduit of the non-collapsible stretchable conduit through the distal end joint and is under control by the PCD unit for negative suctioning; and each said collapsible concentric cylindrical tube-in-tube pressure chamber of the distal end selectively and controllably collapses on negative suctioning of the medium from said pressure chamber by the PCD unit, resulting in shortening of a longitudinal length of said collapsible concentric cylindrical tube-in-tube pressure chamber;

an outermost layer of said non-elastomeric corrugated tubular wall of the distal end is circumferentially surrounded by and glued to a flexible non-corrugated tubular wall; and an innermost tubular chamber of said collapsible concentric cylindrical tube-in-tube pressure chambers of the distal end is a closed space bordered proximally by the distal end joint and distally by the distal end cap.

2. A method for the extensible and guidable endoscopic apparatus for navigation of said endoscopic flexible tubular device in a lumen or a cavity of a living body according to claim 1, wherein said distal end of said endoscopic flexible tubular device is bended by controllably selective decreases in pressure of said medium in at least one of said cylindrical tube-in-tube pressure chambers resulting in longitudinal shortening of at least one of said cylindrical tube-in-tube pressure chambers.

3. The extensible and guidable endoscopic apparatus comprising: an extensive and guidable pressure-sealed endoscopic flexible tubular device, having a proximal end, a distal end, a flexible tubular shaft connecting said proximal and distal ends, a plurality of extension-spring-type coils, a stretchable conduit, a plurality of extensible channels and a medium of gas or liquid filling said endoscopic flexible tubular device, which is configured to be inserted into a lumen or a cavity of a living body to reach a target area; the proximal end, provided in a mechanical and electrical configuration, connected to both said flexible tubular shaft and a power, control and display (PCD) unit, which controls said endoscopic flexible tubular device for longitudinal extension and shortening of said flexible tubular shaft, for pressure mediated bending of said distal end, for delivery of and suctioning of materials to and from said target area, for acquisition and display of visual information and for instrumentation to said target area; the distal end, provided in a mechanical and electrical configuration, having a distal portion of said stretchable conduit, a distal portion of a plurality of said extensible channels, a plurality of non-elastomeric collapsible concentric cylindrical tube-in-tube pressure chambers, a distal end joint, a distal end cap with a solenoid assembly, an image sensor and a light source connected to electric cables, which provides pressure-mediated controllable bending of said distal end, delivery and suctioning of materials to and from the target area, acquisition of visual information and instrumentation to said target area; the flexible tubular shaft, provided in a mechanical configuration, having a non-extensible tubular shaft connected distally and longitudinally in tandem to a reversibly extensible tubular shaft comprising a plurality of reversible extension segments, which provides controllable longitudinal extension and shortening and bending of said reversible extensible tubular shaft; the extension-spring-type coil longitudinally placed inside each reversible extension segment, which provides said reversible extension segment with circumferential structural rigidity, longitudinal flexibility and recoil upon extension; the stretchable conduit comprising electric cables, gas and water channels and pressure conduits, configured in a spiral coil longitudinally and in a concentric honeycomb circumferentially, which runs longitudinally from the PCD unit to the distal end and is longitudinally stretchable, and which delivers gas, water, negative suctioning and electricity to said distal end; the extensible channels, configured in a cylindrically tubular bellows, which runs from the proximal end to the distal end and are longitudinally extensible, and which serve as conduit for longitudinally linear instruments and for delivering materials to the target area; the medium, provided as one or a mixture of gas or of liquid including a gaseous phase of liquid, which fills the entire pressure-sealed internal space of said endoscopic flexible tubular device and is controlled for pressure and volume of said medium by the PCD unit, and which provides said endoscopic flexible tubular device with extension, shortening and bending;

the non-extensible tubular shaft of the flexible tubular shaft, provided as an operating device having a mechanical configuration as a flexible, longitudinally cylindrical tube comprising a non-extensible outer wall and a plurality of internal cylindrical channels, which is connected proximally to the proximal end and to the PCD unit in a Y-shaped configuration, and distally to the proximal side of the reversibly extensible tubular shaft, and which securely aligns and encircles the stretchable conduit and a plurality of the extensible channels;

the internal cylindrical channels of the non-extensible tubular shaft, configured as a plurality of cylindrical channels of concentric cylindrical tube-in-tube along the longitudinal axis, which is connected proximally to the PCD unit and distally to a plurality of the cylindrical channels of the reversible extension segments and is filled with the medium controlled by said PCD unit;

the reversibly extensible tubular shaft of the flexible tubular shaft, provided as an operating device having a mechanical configuration, which comprises a plurality of the reversible extension segments longitudinally attached to each said extension segment via a junction unit, which is connected proximally to the non-extensible tubular shaft and distally to the distal end, and which longitudinally extends and shortens and bends by controllable changes in the pressure and volume of the medium inside said tubular shaft controlled by the PCD unit;

the reversible extension segment of the flexible tubular shaft, provided as an operating device having a plurality of longitudinal internal cylindrical channels in a concentric cylindrical tube-in-tube mechanical configuration, which comprises a plurality of non-elastomeric stretchable corrugated tubular walls with circumferential grooves, the extension-spring-type coil longitudinally placed inside one of said stretchable corrugated tubular walls and the junction unit on each proximal and distal tubular end of said extension segment; and the junction unit of the flexible tubular shaft, provided as an operating device having a mechanical configuration of doughnut-shaped concentric cylindrical tube-in-tube, which provides attachment for the tubular walls and the extension-spring-type coil and regulates flow of the medium to and from the reversible extension segments located on both sides of said junction unit.

4. The extensible and guidable endoscopic apparatus according to claim 3, wherein the non-extensible tubular shaft of the flexible tubular shaft further comprises a plurality of longitudinal cylindrical gaps radially located in each said internal cylindrical channel along the longitudinal axis, which divides said internal cylindrical channel longitudinally into a plurality of evenly separated individual tubular channels.

5. The extensible and guidable endoscopic apparatus according to claim 3, wherein the reversible extension segment of the reversibly extensible tubular shaft in the concentric cylindrical tube-in-tube configuration comprises at least the outer stretchable corrugated wall, the mid stretchable corrugated wall and the inner stretchable corrugated wall, running in parallel with each other along the longitudinal axis, which produces at least three concentrically arranged cylindrical channels, with the outer cylindrical channel formed between the outer and mid stretchable corrugated wall, the mid cylindrical channel between the mid and inner stretchable corrugated wall and the inner central cylindrical channel by the inner stretchable corrugated wall.

6. The extensible and guidable endoscopic apparatus according to claim 5, wherein each of the stretchable corrugated walls of the reversible extension segment comprises a plurality of non-elastomeric thin polymeric sheets adhered together, which has a different tensile direction for axial stretch for each sheet, which has circumferential grooves on an outer surface and an inner surface of said wall for corrugated folding of said wall, and which has multiple linear reinforcement polymer strings embedded in one of said sheets along the longitudinal axis of said reversible extension segment.

7. A method for the extensible and guidable endoscopic apparatus for insertion of said apparatus into a lumen or a cavity to reach a target area of a living body according to claim 5, wherein each said tubular channel of a plurality of said tubular channels longitudinally adjoined side by side maintains a separate set of pressure and volume of said medium to control directional valves of said junction unit.

8. The extensible and guidable endoscopic apparatus according to claim 3, wherein the extension-spring-type coil of the reversible extension segment of the reversibly extensible tubular shaft of the flexible tubular shaft in the concentric cylindrical tube-in-tube configuration is attached to the mid stretchable corrugated wall.

9. The extensible and guidable endoscopic apparatus according to claim 3, wherein the reversible extension segment of the reversibly extensible tubular shaft of the flexible tubular shaft in the concentric cylindrical tube-in-tube configuration further comprises a plurality of longitudinal cylindrical gaps radially located in each said internal cylindrical channel along the longitudinal axis, which divides said internal cylindrical channel longitudinally into a plurality of evenly separated individual tubular channels.

10. The extensible and guidable endoscopic apparatus according to claim 9, wherein the extension-spring-type coil of the reversible extension segment of the reversibly extensible tubular shaft of the flexible tubular shaft in the concentric cylindrical tube-in-tube configuration is fixedly inserted between two said non-elastomeric thin polymeric sheets of the stretchable corrugated mid wall.

11. The extensible and guidable endoscopic apparatus according to claim 3, wherein the junction unit of the flexible tubular shaft comprises an outer cylindrical tube and an inner cylindrical tube that is centrally located inside said outer cylindrical tube;

the outer cylindrical tube and the inner cylindrical tube form a cylindrical chamber, in between of said outer cylindrical tube and said inner cylindrical tube, which is longitudinally divided by a chamber divider in the middle of said cylindrical chamber into an outer junction cylindrical conduit and an inner junction cylindrical conduit; and the outer junction cylindrical conduit and the inner junction cylindrical conduit are matched to the outer cylindrical channel and the inner cylindrical channel, respectively, of said reversible extension segment adjoining said junction unit.

12. The extensible and guidable endoscopic apparatus according to claim 3, wherein the junction unit further comprises:

a directional pressure valve assembly on the proximal side of both the outer and inner junction cylindrical conduits of the junction unit of the flexible tubular shaft, provided as an operating device having a mechanical configuration, which comprises a plurality of radially arranged sets of a directional pressure valve, a valve harness with a valve sealing rim, and a compression spring and a compression spring holder located distally to the valve and centrally aligned with the chamber divider;

the directional pressure valve, provided as an operating device having a mechanical configuration, which is aligned with the chamber divider along the longitudinal axis of said chamber divider, which is releasably fastened to said chamber divider via the compression spring and the compression holder, and which opens and closes the outer and inner cylindrical conduits upon changes in pressure and volume of a medium inside said outer and inner cylindrical conduits provided by the PCD unit;

the compression spring abuts the directional pressure valve proximally and exerts a range of pressure to maintain the directional pressure valve in a closed position;
asymmetric compression of the compression spring tilts the directional pressure valve to an open valve position; and
compressibility of the compression spring can be preset for a range of pressure.

13. The extensible and guidable endoscopic apparatus according to claim 12, wherein
the directional pressure valve, provided in a T-shaped mechanical configuration, comprising a disk facing distally the proximal side of both the outer and inner junction cylindrical conduits at a right angle and a longitudinal bar-shaped stem fixedly connected to a mid portion of a proximal side of the disk;
the disk, provided in a mechanical configuration, which is passively pivotable about the mid portion of said disk in a range of angles to the longitudinal axis of the junction unit by changes in the pressure and volume of the medium in the outer and inner junction cylindrical conduits, which at the right angle to the proximal side of both the outer and inner junction cylindrical conduits closes said proximal side of both the outer and inner junction cylindrical conduits and which pivoted to an acute angle to the longitudinal axis of the junction unit opens the proximal side of either the outer or inner junction cylindrical conduit; and
the longitudinal bar-shaped stem, provided in a mechanical configuration, which is aligned proximally with the mid stretchable corrugated wall of the reversible extension segment, which is passively pivotable about the mid portion of said disk in a range of angles by changes in the pressure and volume of the medium in the outer and inner junction cylindrical conduits, and which maintains a pressure-tight seal with said mid stretchable corrugated wall over a range of pivoted angles of said disk.

14. A method for the extensible and guidable endoscopic apparatus for insertion of said apparatus into a lumen or a cavity to reach a target area of a living body according to claim 12, wherein said directional valves of said junction unit controls flow of said medium to and from said tubular channels by opening and closing said directional valves.

15. A method for the extensible and guidable endoscopic apparatus for insertion of said apparatus into a lumen or a cavity to reach a target area of a living body according to claim 12, wherein said directional valves of said junction unit are opened and closed by changes in pressure and volume of said medium in said tubular channels.

16. A method for the extensible and guidable endoscopic apparatus for insertion of said apparatus into a lumen or a cavity to reach a target area of a living body according to claim 12, wherein an opening pressure and a closing pressure of said directional valve of each junction unit are preset by said compression spring having a preset compressibility of said compression spring for each said directional valve.

17. A method for the extensible and guidable endoscopic apparatus for insertion of said apparatus into a lumen or a cavity to reach a target area of a living body according to claim 12, wherein said endoscopic flexible tubular device is sequentially extended by sequential and selective increases in pressure and volume of said medium in said tubular channels of said reversible extension segments resulting in sequential selective opening and closing of said directional valves at said junction unit.

18. A method for the extensible and guidable endoscopic apparatus for insertion of said apparatus into a lumen or a cavity to reach a target area of a living body according to claim 12, wherein said endoscopic flexible tubular device is extended by repeating the sequence of 'extension of a first reversible extension segment, followed by venting of said medium to a second reversible extension segment and by equalization in pressure and volume of said medium between said first and second reversible extension segments'.

19. A method for the extensible and guidable endoscopic apparatus for insertion of said apparatus into a lumen or a cavity to reach a target area of a living body according to claim 12, wherein said endoscopic flexible tubular device is bended by repeating the sequence of 'bending of a first reversible extension segment, followed by venting of said medium to a second reversible extension segment and by equalization in pressure and volume of said medium between said first and second reversible extension segments'.

20. A method for the extensible and guidable endoscopic apparatus for insertion of said apparatus into a lumen or a cavity to reach a target area of a living body according to claim 12, wherein said endoscopic flexible tubular device is concurrently extended and bended by repeating the sequence of 'extension and bending of a first reversible extension segment, followed by venting of said medium to a second reversible extension segment and by equalization in pressure and volume of said medium between said first and second reversible extension segments'.

21. A method for the extensible and guidable endoscopic apparatus for insertion of said apparatus into a lumen or a cavity to reach a target area of a living body according to claim 3, wherein a portion of said stretchable conduit and extensible channels inside said flexible tubular shaft, running from said PCD unit and from said housings for said extensible channels of said proximal end of said endoscopic flexible tubular device to said reversible extensible tubular shaft, respectively, is made securely aligned and encircled by said non-extensible tubular shaft which is connected distally to said reversible extensible tubular shaft.

22. A method for the extensible and guidable endoscopic apparatus for insertion of said apparatus into a lumen or a cavity to reach a target area of a living body according to claim 3, wherein said reversible extensible shaft is extended and bended by differences in pressure and volume of said medium provided by said PCD unit between said cylindrical compartments produced by said concentric cylindrical tube-in-tube configuration of said reversible extensible shaft.

23. A method for the extensible and guidable endoscopic apparatus for insertion of said apparatus into a lumen or a cavity to reach a target area of a living body according to claim 3, wherein said flexible tubular shaft is made extended and bended in zigzagging directions by longitudinally connected individual reversible extension segments, with each said reversible extension segment longitudinally affixed to a junction unit on both sides of said reversible extension segment and controlled separately by said medium filling in each said reversible extension segment.

24. A method for the extensible and guidable endoscopic apparatus for insertion of said apparatus into a lumen or a cavity to reach a target area of a living body according to claim 3, wherein said PCD unit controllably increases and decreases pressure and volume of said medium in said endoscopic flexible tubular device to longitudinally extend and shorten said endoscopic flexible tubular device, respectively.

25. A method for the extensible and guidable endoscopic apparatus for insertion of said apparatus into a lumen or a cavity to reach a target area of a living body according to claim 3, wherein said PCD unit controllably increases and decreases pressure and volume of said medium in said reversible extension segment to longitudinally extend and shorten said corrugated tubular walls with circumferential grooves of said reversible extension segment, respectively.

26. A method for the extensible and guidable endoscopic apparatus for insertion of said apparatus into a lumen or a cavity to reach a target area of a living body according to claim 3, wherein said PCD unit controllably increases and decreases pressure and volume of said medium in said flexible tubular shaft to stiffen and soften flexibility of said flexible tubular shaft, respectively.

* * * * *